(12) United States Patent
Kinrade et al.

(10) Patent No.: US 7,141,391 B2
(45) Date of Patent: Nov. 28, 2006

(54) MONKEY AND CANINE MELANIN CONCENTRATING HORMONE RECEPTORS

(75) Inventors: Michele Bennet Kinrade, Northford, CT (US); Robbin M. Brodbeck, Madison, CT (US); Stephen M. Waters, Branford, CT (US); James E. Krause, Madison, CT (US)

(73) Assignee: Neurogen Corporation, Branford, CT (US)

( * ) Notice: Subject to any disclaimer, the term of this patent is extended or adjusted under 35 U.S.C. 154(b) by 683 days.

(21) Appl. No.: 10/291,990

(22) Filed: Nov. 12, 2002

(65) Prior Publication Data

US 2003/0148457 A1    Aug. 7, 2003

Related U.S. Application Data

(60) Provisional application No. 60/350,493, filed on Nov. 13, 2001.

(51) Int. Cl.
C07K 14/705    (2006.01)
C07K 19/00     (2006.01)
C12N 15/62     (2006.01)
G01N 33/566    (2006.01)

(52) U.S. Cl. ............... 435/69.7; 435/7.21; 435/252.3; 435/320.1; 530/350; 536/23.4

(58) Field of Classification Search ............... None
See application file for complete search history.

(56) References Cited

U.S. PATENT DOCUMENTS 6,593,108 B1 * 7/2003 Liu et al. ............. 435/69.1

FOREIGN PATENT DOCUMENTS

| WO | WO 00/49046 | 8/2000 |
|----|-------------|--------|
| WO | WO 00/75166 | 12/2000 |
| WO | WO 01/05947 | 1/2001 |
| WO | WO 01/07606 | 2/2001 |
| WO | WO 01/36479 | 5/2001 |
| WO | WO 01/68706 | 9/2001 |
| WO | WO 01/70975 | 9/2001 |
| WO | WO 02/03070 | 1/2002 |
| WO | WO 02/08290 | 1/2002 |
| WO | WO 02/36076 | 5/2002 |
| WO | WO 02/097394 | 12/2002 |

OTHER PUBLICATIONS

Buggy et al. "Glucagon-Glucagon-like Peptide I Receptor Chimeras Reveal Domains That Determine Specificity of Glucagon Binding", Mar. 1995, J. Biol. Chem. 270(13):7474-7478.*
Holtmann et al. "Critical Contributions of Amino-terminal Extracellular Domains in Agonist Binding and Activation of Secretin and Vasoactive Intesinal Polypeptide Receptors", Jun. 16, 1995, J. Biol. Chem. 270(24):14394-14398.*
Kim et al. "Random Chimeragenesis of G protein-coupled Receptors", Nov. 18, 1994, J. Biol. Chem. 269(46):28724-28731.*
Meng et al. "Mapping the Receptor Domains Critical for the Binding Selectivity of delta-opioid Receptor Ligands", 1996, Euro. J. Pharmacol. 311:285-292.*
Schioth et al., "Chimeric Melatonin MC1 and MC3 Receptors: Identification of domains Participating in Binding of Melanocyte-Stimulating Hormone Peptides", 1998, Mol. Pharmacol. 54:154-161.*
Takagi et al. "Structural Basis of G Protein Specificity of Human Endothelial Receptors", Aug. 28, 1995, J. Biol. Chem. 270(17):10072-10078.*
Gether et al. "Chimeric NK1 (Substance P)/NK3(Neuromedin B) Receptors", Apr. 15, 1993, J. Biol. Chem. 268(11):7893-7898.*
Wu et al. "First Intracellular Loop of the Human Cholecystokinin-A Receptor Is Essential for Cyclic AMP Signalling in Transfected HEK-293 Cells", Apr. 4, 1997, J. Biol. Chem. 272(14):9037-9042.*
Rodriguez et al., "Cloning and Molecular Characterization of the Novel Human Melanin-Concentrating Hormone Receptor MCH2," Mol. Pharmacol. (2001) 60:632-639.
An et al., "Identification and characterization of a melanin concentrating hormone receptor," Proc. Natl. Acad. Sci. USA (2001) 98:7576-7581.
Sailer et al., "Identification and characterization of a second melanin concentrating hormone receptor, MCH-2R," Proc. Natl. Acad. Sci. USA (2001) 98:7564-7569.
Mori et al., "Cloning of a Novel G Protein-Coupled Receptor, SLT, a Subtype of the Melanin-Concentrating Hormone Receptor," Biochem. Biophys. Res. Comm. (2001) 283:1013-1018.
Hill et al., "Molecular Cloning and Functional Characterization of $MCH_2$, a Novel Human MCH Receptor," J. Biol. Chem. (2001) 276:20125-20129.
Chambers et al., "Melanin-concentrating hormone is the cognate ligand for the orphan G-protein-coupled receptor SLC-1," Nature (1999) 400:261-265.
Saito et al., "Molecular characterization of the melanin-concentrating-hormone receptor," Nature (1999) 400:265-269.
Lakaye et al., "Cloning of the rat brain cDNA encoding for the SLC-1 G protein-coupled receptor reveals the presence of an intron in the gene," Biochimica et Biophysica Acta (1998) 1401:215-220.
Kolakowski et al., "Characterization of a human gene related to genes encoding somatostatin receptors," FEBS Letters (1996) 398:253-258.

* cited by examiner

*Primary Examiner*—John Ulm
(74) *Attorney, Agent, or Firm*—Ann T. Kadlecek; Seth A. Fidel

(57) ABSTRACT

Isolated polynucleotides encoding monkey and canine Melanin Concentrating Hormone (MCH) Type 2 receptors and chimeric polypeptides are provided. Vectors and cells for recombinant expression of such MCH receptor polypeptides, and isolated MCH receptor polypeptides are also provided. MCH receptor polynucleotides and polypeptides may be used, for example, to identify agents that specifically interact with MCH receptor. Such agents find use within therapies for humans and animals afflicted with conditions associated with MCH receptor activation.

15 Claims, 4 Drawing Sheets

MCH2 Receptors Aligned

```
        1.........10........20.........30..........40
hMCH2R  MNPFHASCWN TSAELLNKSW NKEFAYQTAS VVDTVILPSM
mMCH2RA MNPFHSSCWN TSAELSNKSW NKEFAYQTAS VVDTVILPSM
mMCH2RB MNPFHSSCWN TSAELSNKSW NKEFAYQTAS VVDTVILLSM
cMCH2R  MYSLHSSCWN TSAEPLNKSC NKEFAYHTLS ILDTIILPSM

.........50.........60.........70..........80
hMCH2R  IGIICSTGLV GNILIVFTII RSRKKTVPDI YICNLAVADL
mMCH2RA IGIICSTGLV GNILIVFTII RSRKKTVPDI YICNLAVADL
mMCH2RB IGIICSTGLV GNILIVFTII RSRKKTVPDI YICNLAVADL
cMCH2R  IGIICSNGLV GNILIVFTII RSRKKTIPDI YICNLAVADL

.........90........100.........110.........120
hMCH2R  VHIVGMPFLI HQWARGGEWV FGGPLCTIIT SLDTCNQFAC
mMCH2RA VHIVGMPFLI HQWARGGEWV FGGPLCTIIT SLDTCNQFAC
mMCH2RB VHIVGMPFLI HQWARGGEWV FGGPLCTIIT SLDTCNQFAC
cMCH2R  VHIIGMPFLI HQWARGGEWV FGGPLCTIIT SLDTCNQFAC

.........130.........140.........150.........160
hMCH2R  SAIMTVMSVD RYFALVQPFR LTRWRTRYKT IRINLGLWAA
mMCH2RA SAIMTVMSVD RYFALVQPFR LTSWRTRYKT IRINLGLWAA
mMCH2RB SAIMTVMSVD RYFALVQPFR LTSWRTRYKT IRINLGLWAA
cMCH2R  SAIMTVMSID RYLALVQPFR LTSWRTRYKT IRINLGLWAA
```

Figure 1A

```
          ........130........140........150........160
hMCH2R    SAIMTVMSVD RYFALVQPFR LTRWRTRYKT IRINLGLWAA
mMCH2RA   SAIMTVMSVD RYFALVQPFR LTSWRTRYKT IRINLGLWAA
mMCH2RB   SAIMTVMSVD RYFALVQPFR LTSWRTRYKT IRINLGLWAA
cMCH2R    SAIMTVMSID RYLALVQPFR LTSWRTRYKT IRINLGLWAA

........170........180........190........200
hMCH2R    SFILALPVWV YSKVIKFKDG VESCAFDLTS PDDVLWYTLY
mMCH2RA   SFILALPVWI YSKVIKFKDG VESCAFDLTS PDDVLWYTLY
mMCH2RB   SFILALPVWI YSKVIKFKDG VESCAFDLTS PDDVLWYTLY
cMCH2R    SFILALPVWV YSKVIKFKDG VESCAFDLTS PDDVLRYTLY

........210........220........230........240
hMCH2R    LTITTFFFPL PLILVCYILI LCYTWEMYQQ NKDARCCNPS
mMCH2RA   LTITTFFFPL PLILVCYILI LCYTWEMYQQ NKDARCCNPS
mMCH2RB   LTITTFFFPL PLILVCYILI LCYTWEMYQQ NKDARCCNPS
cMCH2R    LTITTFFFPL PLILVCYILI LCYTWEMYQQ NKDARCYNPS

........250........260........270........280
hMCH2R    VPKQRVMKLT KMVLVLVVVF ILSAAPYHVI QLVNLQMEQP
mMCH2RA   VPKQRVMKLT KMVLVLVAVF ILSAAPYHVI QLVNLQMEQP
mMCH2RB   VPKQRVMKLT KMVLVLVAVF ILSAAPYHVI QLVNLQMEQP
cMCH2R    VPKERVMKLT KMVLVLVAVF ILSAAPYHVI QLVNLKMQQP
```

Figure 1B

```
                  . . . . . . . . . . 290. . . . . . . . . . 300. . . . . . . . . . 310. . . . . . . . . . 320
hMCH2R    T L A F Y V G Y Y L    S I C L S Y A S S S    I N P F L Y I L L S    G N F Q K R L P Q I mMCH2RA   T L A F Y V G Y Y L    S I C L S Y A S S S    I N P F L Y I L L S    G N F Q K R L P Q I mMCH2RB   T L A F Y V G Y Y L    S I C L S Y A S S S    I N P F L Y I L L S    G N F Q K R L P Q I cMCH2R    T L A F H V G Y Y L    S I C F S Y A S S S    I N P F L Y I M L S    G N F R K R L P Q V

. . . . . . . . . . 330. . . . . . . . . . 340. . . . . . . . . . 350. . . . . . . . . . 360
hMCH2R    Q R R A T E K E I N    N M G N T L K S H F mMCH2RA   Q R R V T D K E I K    N M G N T L K S H F mMCH2RB   Q R R V T D K E I K    N M G N T L K S H F cMCH2R    Q R R V T E K S T I
```

Figure 1C

SEQUENCE LISTING

<160> NUMBER OF SEQ ID NOS: 34

<210> SEQ ID NO 1
<211> LENGTH: 1023
<212> TYPE: DNA
<213> ORGANISM: Macaca fascicularis

<400> SEQUENCE: 1

```
atgaatccat tcactcatc ttgttggaac acctctgccg aactttcaaa caaatcctgg      60
aataaagagt ttgcttatca aactgccagt gttgtagata cagtcatcct cccttccatg    120
attgggatta tctgttcaac agggctggtt ggcaacatcc tcattgtatt cactataata    180
aggtccagaa aaaaaacagt ccctgacatc tatatctgca acctggctgt ggctgatttg    240
gtccacatcg ttggaatgcc ttttcttatt caccagtggg cccgaggggg agagtgggta    300
tttgggggc ctctctgcac catcatcaca tccctgata cttgtaacca atttgcctgt      360
agtgccatca tgactgtaat gagtgtggac aggtactttg ccctcgtcca accatttcga    420
ctgacgagtt ggaggacaag gtacaagacc atccggatca atttgggcct ttgggcagct    480
tcctttatcc tggcattgcc tgtctggatc tactcgaagg tcatcaaatt taaagacggt    540
gtcgagagtt gtgcttttga tttgacatcc cctgacgatg tactctggta tacactttat    600
ttgacaataa caactttctt tttccctcta cccttgattt tggtgtgcta tattttaatt    660
ttatgctata cttgggagat gtatcaacag aataaggatg ccagatgttg caatcccagc    720
gtaccaaaac agagagtgat gaagttgaca aagatggtgc tggtgctggt ggcagtcttt    780
atcctaagtg ctgcccctta tcatgtgata caactggtga acttacagat ggaacagccc    840
acactggcct tctatgtggg ttattacctc tccatctgtc tcagctatgc cagcagcagc    900
attaaccctt ttctctacat cctgctgagt ggaaatttcc agaaacgtct gcctcaaatc    960
caaaggagag tgactgacaa ggaaatcaaa aatatgggaa acactctgaa atcacacttt   1020
tag                                                                 1023
```

<210> SEQ ID NO 2
<211> LENGTH: 340
<212> TYPE: PRT
<213> ORGANISM: Macaca fascicularis

<400> SEQUENCE: 2

```
Met Asn Pro Phe His Ser Ser Cys Trp Asn Thr Ser Ala Glu Leu Ser
1               5                   10                  15

Asn Lys Ser Trp Asn Lys Glu Phe Ala Tyr Gln Thr Ala Ser Val Val
            20                  25                  30

Asp Thr Val Ile Leu Pro Ser Met Ile Gly Ile Ile Cys Ser Thr Gly
        35                  40                  45

Leu Val Gly Asn Ile Leu Ile Val Phe Thr Ile Ile Arg Ser Arg Lys
    50                  55                  60

Lys Thr Val Pro Asp Ile Tyr Ile Cys Asn Leu Ala Val Ala Asp Leu
65                  70                  75                  80

Val His Ile Val Gly Met Pro Phe Leu Ile His Gln Trp Ala Arg Gly
                85                  90                  95

Gly Glu Trp Val Phe Gly Gly Pro Leu Cys Thr Ile Ile Thr Ser Leu
            100                 105                 110

Asp Thr Cys Asn Gln Phe Ala Cys Ser Ala Ile Met Thr Val Met Ser
        115                 120                 125
```

Val Asp Arg Tyr Phe Ala Leu Val Gln Pro Phe Arg Leu Thr Ser Trp
130                 135                 140

Arg Thr Arg Tyr Lys Thr Ile Arg Ile Asn Leu Gly Leu Trp Ala Ala
145                 150                 155                 160

Ser Phe Ile Leu Ala Leu Pro Val Trp Ile Tyr Ser Lys Val Ile Lys
                165                 170                 175

Phe Lys Asp Gly Val Glu Ser Cys Ala Phe Asp Leu Thr Ser Pro Asp
            180                 185                 190

Asp Val Leu Trp Tyr Thr Leu Tyr Leu Thr Ile Thr Thr Phe Phe Phe
                195                 200                 205

Pro Leu Pro Leu Ile Leu Val Cys Tyr Ile Leu Ile Leu Cys Tyr Thr
            210                 215                 220

Trp Glu Met Tyr Gln Gln Asn Lys Asp Ala Arg Cys Cys Asn Pro Ser
225                 230                 235                 240

Val Pro Lys Gln Arg Val Met Lys Leu Thr Lys Met Val Leu Val Leu
                245                 250                 255

Val Ala Val Phe Ile Leu Ser Ala Ala Pro Tyr His Val Ile Gln Leu
            260                 265                 270

Val Asn Leu Gln Met Glu Gln Pro Thr Leu Ala Phe Tyr Val Gly Tyr
            275                 280                 285

Tyr Leu Ser Ile Cys Leu Ser Tyr Ala Ser Ser Ile Asn Pro Phe
            290                 295                 300

Leu Tyr Ile Leu Leu Ser Gly Asn Phe Gln Lys Arg Leu Pro Gln Ile
305                 310                 315                 320

Gln Arg Arg Val Thr Asp Lys Glu Ile Lys Asn Met Gly Asn Thr Leu
                325                 330                 335

Lys Ser His Phe
            340

<210> SEQ ID NO 3
<211> LENGTH: 1023
<212> TYPE: DNA
<213> ORGANISM: Macaca fascicularis

<400> SEQUENCE: 3

```
atgaatccat tcactcatc ttgttggaac acctctgccg aactttcaaa caaatcctgg      60
aataaagagt ttgcttatca aactgccagt gttgtagata cagtcatcct cctttccatg    120
attgggatta tctgttcaac agggctggtt ggcaacatcc tcattgtatt cactataata    180
aggtccagaa aaaaaacagt ccctgacatc tatatctgca acctggctgt ggctgatttg    240
gtccacatcg ttggaatgcc tttttcttatt caccagtggg cccgaggggg agagtgggta    300
tttgggggc ctctctgcac catcatcaca tccctggata cttgtaacca atttgcctgt    360
agtgccatca tgactgtaat gagtgtggac aggtactttg ccctcgtcca accatttcga    420
ctgacgagtt ggaggacaag gtacaagacc atccggatca atttgggcct tgggcagct    480
tcctttatcc tggcattgcc tgtctggatc tactcgaagg tcatcaaatt taaagacggt    540
gtcgagagtt gtgcttttga tttgacatcc cctgacgatg tactctggta tacactttat    600
ttgacaataa caacttttctt tttccctcta cccttgattt tggtgtgcta tattttaatt    660
ttatgctata cttgggagat gtatcaacag aataaggatg ccagatgttg caatcccagc    720
gtaccaaaac agagagtgat gaagttgaca aagatggtgc tggtgctggt ggcagtctttt  780
atcctaagtg ctgccccctta tcatgtgata caactggtga acttacagat ggaacagccc    840
```

-continued

```
acactggcct tctatgtggg ttattacctc tccatctgtc tcagctatgc cagcagcagc    900
attaaccctt ttctctacat cctgctgagt ggaaatttcc agaaacgtct gcctcaaatc    960
caaaggagag tgactgacaa ggaaatcaaa aatatgggaa acactctgaa atcacacttt   1020
tag                                                                 1023
```

<210> SEQ ID NO 4
<211> LENGTH: 340
<212> TYPE: PRT
<213> ORGANISM: Macaca fascicularis

<400> SEQUENCE: 4

```
Met Asn Pro Phe His Ser Ser Cys Trp Asn Thr Ser Ala Glu Leu Ser
1               5                   10                  15

Asn Lys Ser Trp Asn Lys Glu Phe Ala Tyr Gln Thr Ala Ser Val Val
            20                  25                  30

Asp Thr Val Ile Leu Leu Ser Met Ile Gly Ile Ile Cys Ser Thr Gly
        35                  40                  45

Leu Val Gly Asn Ile Leu Ile Val Phe Thr Ile Ile Arg Ser Arg Lys
    50                  55                  60

Lys Thr Val Pro Asp Ile Tyr Ile Cys Asn Leu Ala Val Ala Asp Leu
65                  70                  75                  80

Val His Ile Val Gly Met Pro Phe Leu Ile His Gln Trp Ala Arg Gly
                85                  90                  95

Gly Glu Trp Val Phe Gly Gly Pro Leu Cys Thr Ile Ile Thr Ser Leu
            100                 105                 110

Asp Thr Cys Asn Gln Phe Ala Cys Ser Ala Ile Met Thr Val Met Ser
        115                 120                 125

Val Asp Arg Tyr Phe Ala Leu Val Gln Pro Phe Arg Leu Thr Ser Trp
    130                 135                 140

Arg Thr Arg Tyr Lys Thr Ile Arg Ile Asn Leu Gly Leu Trp Ala Ala
145                 150                 155                 160

Ser Phe Ile Leu Ala Leu Pro Val Trp Ile Tyr Ser Lys Val Ile Lys
                165                 170                 175

Phe Lys Asp Gly Val Glu Ser Cys Ala Phe Asp Leu Thr Ser Pro Asp
            180                 185                 190

Asp Val Leu Trp Tyr Thr Leu Tyr Leu Thr Ile Thr Thr Phe Phe Phe
        195                 200                 205

Pro Leu Pro Leu Ile Leu Val Cys Tyr Ile Leu Ile Leu Cys Tyr Thr
    210                 215                 220

Trp Glu Met Tyr Gln Gln Asn Lys Asp Ala Arg Cys Cys Asn Pro Ser
225                 230                 235                 240

Val Pro Lys Gln Arg Val Met Lys Leu Thr Lys Met Val Leu Val Leu
                245                 250                 255

Val Ala Val Phe Ile Leu Ser Ala Ala Pro Tyr His Val Ile Gln Leu
            260                 265                 270

Val Asn Leu Gln Met Glu Gln Pro Thr Leu Ala Phe Tyr Val Gly Tyr
        275                 280                 285

Tyr Leu Ser Ile Cys Leu Ser Tyr Ala Ser Ser Ile Asn Pro Phe
    290                 295                 300

Leu Tyr Ile Leu Leu Ser Gly Asn Phe Gln Lys Arg Leu Pro Gln Ile
305                 310                 315                 320

Gln Arg Arg Val Thr Asp Lys Glu Ile Lys Asn Met Gly Asn Thr Leu
                325                 330                 335
```

Lys Ser His Phe
                340

<210> SEQ ID NO 5
<211> LENGTH: 1023
<212> TYPE: DNA
<213> ORGANISM: Macaca fascicularis

<400> SEQUENCE: 5

| | | | | | |
|---|---|---|---|---|---|
| atgaatccat | tcactcatc | ttgttggaac | acctctgccg | aactttcaaa | caaatcctgg | 60 |
| aataaagagt | tgcttatca | aactgccagt | gttgtagata | cagtcatcct | cccttccatg | 120 |
| attgggatta | tctgttcaac | agggctggtt | ggcaacatcc | tcattgtatt | cactataata | 180 |
| aggtccagaa | aaaaacagt | ccctgacatc | tatatctgca | acctggctgt | ggctgatttg | 240 |
| gtccacatcg | ttggaatgcc | ttttcttatt | caccagtggg | cccgaggggg | agagtgggta | 300 |
| tttgggggc | ctctctgcac | catcatcaca | tccctggata | cttgtaacca | atttgcctgt | 360 |
| agtgccatca | tgactgtaat | gagtgtggac | aggtactttg | ccctcgtcca | accatttcga | 420 |
| ctgacaagtt | ggagaacaag | gtacaagacc | atccggatca | atttgggcct | ttgggcagct | 480 |
| tcctttatcc | tggcattgcc | tgtctggatc | tactcgaagg | tcatcaaatt | taaagacggt | 540 |
| gtcgagagtt | gtgcttttga | tttgacatcc | cctgacgatg | tactctggta | tacactttat | 600 |
| ttgacaataa | caactttctt | tttccctcta | cccttgattt | tggtgtgcta | tatttttaatt | 660 |
| ttatgctata | cttgggagat | gtatcaacag | aataaggatg | ccagatgttg | caatcccagc | 720 |
| gtaccaaaac | agagagtgat | gaagttgaca | agatggtgc | tggtgctggt | ggcagtcttt | 780 |
| atcctaagtg | ctgcccctta | tcatgtgata | caactggtga | acttacagat | ggaacagccc | 840 |
| acactggcct | tctatgtggg | ttattacctc | tccatctgtc | tcagctatgc | cagcagcagc | 900 |
| attaaccctt | ttctctacat | cctgctgagt | ggaaatttcc | agaaacgtct | gcctcaaatc | 960 |
| caaaggagag | tgactgacaa | ggaaatcaaa | atatgggaa | acactctgaa | atcacacttt | 1020 |
| tag | | | | | | 1023 |

<210> SEQ ID NO 6
<211> LENGTH: 993
<212> TYPE: DNA
<213> ORGANISM: Canis sp.

<400> SEQUENCE: 6

| | | | | | |
|---|---|---|---|---|---|
| atgtattcac | ttcactcatc | ctgttggaac | acctctgctg | aacctttgaa | caaatcctgc | 60 |
| aataaagagt | tgcttatca | caccctcagc | attttagata | caatcatcct | cccttctatg | 120 |
| attgggatta | tctgttcaat | ggggctagtt | ggcaacatcc | tcattgtatt | cactataata | 180 |
| aggtccagga | aaaaaaccat | tcctgacatt | tatatctgca | acctggctgt | ggctgatctg | 240 |
| gtccacatca | ttggaatgcc | atttcttatt | catcagtggg | cccggggagg | agagtgggtg | 300 |
| tttgggggc | ccctctgcac | cattatcaca | tccctggata | cctgcaacca | gtttgcctgt | 360 |
| agtgccatca | tgactgtgat | gagtatagac | aggtacttgg | ctctcgtcca | accatttcga | 420 |
| cttacaagtt | ggagaacgag | gtacaagacc | atccgcatca | atttgggcct | ttgggcagct | 480 |
| tccttcattc | tggcgctgcc | tgtctgggtc | tactcgaagg | tcatcaaatt | taaagacggc | 540 |
| gtggagagtt | gtgcttttga | tttaacatcc | cctgacgatg | tactccggta | tacactttat | 600 |
| ttgacgataa | caactttttt | tttcccttg | cctttgattt | tggtgtgcta | tattttaatt | 660 |
| ttatgctata | cttgggagat | gtatcaacag | aataaagatg | caagatgtta | caatcccagt | 720 |

```
gttccaaaag agagagtgat gaagctgaca aagatggtgc tggtgctggt ggcggtcttt    780
atcctaagtg ctgcccccta ccacgtgata caactggtga acttaaagat gcagcagccc    840
acactggcct tccatgtagg ctattatctc tccatctgtt tcagctatgc cagcagcagc    900
attaacccct tcctctacat catgctgagt ggaaatttcc ggaaacgcct acctcaagta    960
caaaggagag tgactgagaa atcaacaata tag                                 993
```

<210> SEQ ID NO 7
<211> LENGTH: 330
<212> TYPE: PRT
<213> ORGANISM: Canis sp.

<400> SEQUENCE: 7

```
Met Tyr Ser Leu His Ser Ser Cys Trp Asn Thr Ser Ala Glu Pro Leu
1               5                   10                  15

Asn Lys Ser Cys Asn Lys Glu Phe Ala Tyr His Thr Leu Ser Ile Leu
            20                  25                  30

Asp Thr Ile Ile Leu Pro Ser Met Ile Gly Ile Ile Cys Ser Met Gly
        35                  40                  45

Leu Val Gly Asn Ile Leu Ile Val Phe Thr Ile Ile Arg Ser Arg Lys
50                  55                  60

Lys Thr Ile Pro Asp Ile Tyr Ile Cys Asn Leu Ala Val Ala Asp Leu
65                  70                  75                  80

Val His Ile Ile Gly Met Pro Phe Leu Ile His Gln Trp Ala Arg Gly
                85                  90                  95

Gly Glu Trp Val Phe Gly Gly Pro Leu Cys Thr Ile Ile Thr Ser Leu
            100                 105                 110

Asp Thr Cys Asn Gln Phe Ala Cys Ser Ala Ile Met Thr Val Met Ser
        115                 120                 125

Ile Asp Arg Tyr Leu Ala Leu Val Gln Pro Phe Arg Leu Thr Ser Trp
    130                 135                 140

Arg Thr Arg Tyr Lys Thr Ile Arg Ile Asn Leu Gly Leu Trp Ala Ala
145                 150                 155                 160

Ser Phe Ile Leu Ala Leu Pro Val Trp Val Tyr Ser Lys Val Ile Lys
                165                 170                 175

Phe Lys Asp Gly Val Glu Ser Cys Ala Phe Asp Leu Thr Ser Pro Asp
            180                 185                 190

Asp Val Leu Arg Tyr Thr Leu Tyr Leu Thr Ile Thr Thr Phe Phe Phe
        195                 200                 205

Pro Leu Pro Leu Ile Leu Val Cys Tyr Ile Leu Ile Leu Cys Tyr Thr
    210                 215                 220

Trp Glu Met Tyr Gln Gln Asn Lys Asp Ala Arg Cys Tyr Asn Pro Ser
225                 230                 235                 240

Val Pro Lys Glu Arg Val Met Lys Leu Thr Lys Met Val Leu Val Leu
                245                 250                 255

Val Ala Val Phe Ile Leu Ser Ala Ala Pro Tyr His Val Ile Gln Leu
            260                 265                 270

Val Asn Leu Lys Met Gln Gln Pro Thr Leu Ala Phe His Val Gly Tyr
        275                 280                 285

Tyr Leu Ser Ile Cys Phe Ser Tyr Ala Ser Ser Ile Asn Pro Phe
    290                 295                 300

Leu Tyr Ile Met Leu Ser Gly Asn Phe Arg Lys Arg Leu Pro Gln Val
305                 310                 315                 320

Gln Arg Arg Val Thr Glu Lys Ser Thr Ile
                325                 330
```

<210> SEQ ID NO 8
<211> LENGTH: 24
<212> TYPE: DNA
<213> ORGANISM: artificial sequence
<220> FEATURE:
<223> OTHER INFORMATION: 5' forward outer primer

<400> SEQUENCE: 8
tccctggaaa ggccacgaac aatg                                    24

<210> SEQ ID NO 9
<211> LENGTH: 22
<212> TYPE: DNA
<213> ORGANISM: artificial sequence
<220> FEATURE:
<223> OTHER INFORMATION: 879R reverse primer

<400> SEQUENCE: 9
cagcaccagc accatctttg tc                                      22

<210> SEQ ID NO 10
<211> LENGTH: 22
<212> TYPE: DNA
<213> ORGANISM: artificial sequence
<220> FEATURE:
<223> OTHER INFORMATION: 509 forward primer

<400> SEQUENCE: 10
ttgccctcgt ccaaccattt cg                                      22

<210> SEQ ID NO 11
<211> LENGTH: 21
<212> TYPE: DNA
<213> ORGANISM: artificial sequence
<220> FEATURE:
<223> OTHER INFORMATION: 3' reverse outer primer

<400> SEQUENCE: 11
ggtgatccat gtactttcct a                                       21

<210> SEQ ID NO 12
<211> LENGTH: 39
<212> TYPE: DNA
<213> ORGANISM: artificial sequence
<220> FEATURE:
<223> OTHER INFORMATION: 5' Kozak cloning primer

<400> SEQUENCE: 12
cgcggatcca ccatgaatcc atttcactca tcttgttgg                    39

<210> SEQ ID NO 13
<211> LENGTH: 6
<212> TYPE: PRT
<213> ORGANISM: artificial sequence
<220> FEATURE:
<223> OTHER INFORMATION: His 6x epitope

<400> SEQUENCE: 13

His His His His His His
1               5

<210> SEQ ID NO 14
<211> LENGTH: 8
<212> TYPE: PRT

<213> ORGANISM: artificial sequence
<220> FEATURE:
<223> OTHER INFORMATION: FLAG epitope

<400> SEQUENCE: 14

Asp Tyr Lys Asp Asp Asp Lys
1               5

<210> SEQ ID NO 15
<211> LENGTH: 348
<212> TYPE: PRT
<213> ORGANISM: artificial sequence
<220> FEATURE:
<223> OTHER INFORMATION: Cynomolgus macaque MCH2R/MCH1R C-terminal
      chimera A

<400> SEQUENCE: 15

Met Asn Pro Phe His Ser Ser Cys Trp Asn Thr Ser Ala Glu Leu Ser
1               5                   10                  15

Asn Lys Ser Trp Asn Lys Glu Phe Ala Tyr Gln Thr Ala Ser Val Val
            20                  25                  30

Asp Thr Val Ile Leu Pro Ser Met Ile Gly Ile Ile Cys Ser Thr Gly
        35                  40                  45

Leu Val Gly Asn Ile Leu Ile Val Phe Thr Ile Arg Ser Arg Lys
    50                  55                  60

Lys Thr Val Pro Asp Ile Tyr Ile Cys Asn Leu Ala Val Ala Asp Leu
65                  70                  75                  80

Val His Ile Val Gly Met Pro Phe Leu Ile His Gln Trp Ala Arg Gly
                85                  90                  95

Gly Glu Trp Val Phe Gly Gly Pro Leu Cys Thr Ile Ile Thr Ser Leu
            100                 105                 110

Asp Thr Cys Asn Gln Phe Ala Cys Ser Ala Ile Met Thr Val Met Ser
        115                 120                 125

Val Asp Arg Tyr Phe Ala Leu Val Gln Pro Phe Arg Leu Thr Ser Trp
130                 135                 140

Arg Thr Arg Tyr Lys Thr Ile Arg Ile Asn Leu Gly Leu Trp Ala Ala
145                 150                 155                 160

Ser Phe Ile Leu Ala Leu Pro Val Trp Ile Tyr Ser Lys Val Ile Lys
                165                 170                 175

Phe Lys Asp Gly Val Glu Ser Cys Ala Phe Asp Leu Thr Ser Pro Asp
            180                 185                 190

Asp Val Leu Trp Tyr Thr Leu Tyr Leu Thr Ile Thr Thr Phe Phe Phe
        195                 200                 205

Pro Leu Pro Leu Ile Leu Val Cys Tyr Ile Leu Ile Leu Cys Tyr Thr
    210                 215                 220

Trp Glu Met Tyr Gln Gln Asn Lys Asp Ala Arg Cys Cys Asn Pro Ser
225                 230                 235                 240

Val Pro Lys Gln Arg Val Met Lys Leu Thr Lys Met Val Leu Val Leu
                245                 250                 255

Val Ala Val Phe Ile Leu Ser Ala Ala Pro Tyr His Val Ile Gln Leu
            260                 265                 270

Val Asn Leu Gln Met Glu Gln Pro Thr Leu Ala Phe Tyr Val Gly Tyr
        275                 280                 285

Tyr Leu Ser Ile Cys Leu Ser Tyr Ala Ser Ser Ser Ile Asn Pro Phe
    290                 295                 300

Leu Tyr Ile Leu Leu Ser Gly Asn Phe Gln Lys Arg Leu Val Leu Ser
305                 310                 315                 320

Val Lys Pro Ala Ala Gln Gly Gln Leu Arg Ala Val Ser Asn Ala Gln
            325                 330                 335

Thr Ala Asp Glu Glu Arg Thr Glu Ser Lys Gly Thr
            340                 345

<210> SEQ ID NO 16
<211> LENGTH: 348
<212> TYPE: PRT
<213> ORGANISM: artificial sequence
<220> FEATURE:
<223> OTHER INFORMATION: Cynomolgus macaque MCH2R/MCH1R C-terminal
      chimera B

<400> SEQUENCE: 16

Met Asn Pro Phe His Ser Ser Cys Trp Asn Thr Ser Ala Glu Leu Ser
1               5                   10                  15

Asn Lys Ser Trp Asn Lys Glu Phe Ala Tyr Gln Thr Ala Ser Val Val
            20                  25                  30

Asp Thr Val Ile Leu Pro Ser Met Ile Gly Ile Ile Cys Ser Thr Gly
        35                  40                  45

Leu Val Gly Asn Ile Leu Ile Val Phe Thr Ile Ile Arg Ser Arg Lys
    50                  55                  60

Lys Thr Val Pro Asp Ile Tyr Ile Cys Asn Leu Ala Val Ala Asp Leu
65                  70                  75                  80

Val His Ile Val Gly Met Pro Phe Leu Ile His Gln Trp Ala Arg Gly
                85                  90                  95

Gly Glu Trp Val Phe Gly Gly Pro Leu Cys Thr Ile Ile Thr Ser Leu
            100                 105                 110

Asp Thr Cys Asn Gln Phe Ala Cys Ser Ala Ile Met Thr Val Met Ser
        115                 120                 125

Val Asp Arg Tyr Phe Ala Leu Val Gln Pro Phe Arg Leu Thr Ser Trp
    130                 135                 140

Arg Thr Arg Tyr Lys Thr Ile Arg Ile Asn Leu Gly Leu Trp Ala Ala
145                 150                 155                 160

Ser Phe Ile Leu Ala Leu Pro Val Trp Ile Tyr Ser Lys Val Ile Lys
                165                 170                 175

Phe Lys Asp Gly Val Glu Ser Cys Ala Phe Asp Leu Thr Ser Pro Asp
            180                 185                 190

Asp Val Leu Trp Tyr Thr Leu Tyr Leu Thr Ile Thr Thr Phe Phe Phe
        195                 200                 205

Pro Leu Pro Leu Ile Leu Val Cys Tyr Ile Leu Ile Leu Cys Tyr Thr
    210                 215                 220

Trp Glu Met Tyr Gln Gln Asn Lys Asp Ala Arg Cys Cys Asn Pro Ser
225                 230                 235                 240

Val Pro Lys Gln Arg Val Met Lys Leu Thr Lys Met Val Leu Val Leu
                245                 250                 255

Val Ala Val Phe Ile Leu Ser Ala Ala Pro Tyr His Val Ile Gln Leu
            260                 265                 270

Val Asn Leu Gln Met Glu Gln Pro Thr Leu Ala Phe Tyr Val Gly Tyr
        275                 280                 285

Tyr Leu Ser Ile Cys Leu Ser Tyr Ala Ser Ser Ile Asn Pro Phe
    290                 295                 300

Leu Tyr Ile Leu Leu Ser Gly Asn Phe Arg Lys Arg Leu Val Leu Ser
305                 310                 315                 320

Val Lys Pro Ala Ala Gln Gly Gln Leu Arg Ala Val Ser Asn Ala Gln

```
                        325                 330                 335
Thr Ala Asp Glu Glu Arg Thr Glu Ser Lys Gly Thr
            340                 345

<210> SEQ ID NO 17
<211> LENGTH: 330
<212> TYPE: PRT
<213> ORGANISM: artificial sequence
<220> FEATURE:
<223> OTHER INFORMATION: Cynomolgus macaque MCH2R/canine MCH2R
      C-terminal chimera A

<400> SEQUENCE: 17

Met Asn Pro Phe His Ser Ser Cys Trp Asn Thr Ser Ala Glu Leu Ser
1               5                   10                  15

Asn Lys Ser Trp Asn Lys Glu Phe Ala Tyr Gln Thr Ala Ser Val Val
            20                  25                  30

Asp Thr Val Ile Leu Pro Ser Met Ile Gly Ile Ile Cys Ser Thr Gly
        35                  40                  45

Leu Val Gly Asn Ile Leu Ile Val Phe Thr Ile Ile Arg Ser Arg Lys
    50                  55                  60

Lys Thr Val Pro Asp Ile Tyr Ile Cys Asn Leu Ala Val Ala Asp Leu
65                  70                  75                  80

Val His Ile Val Gly Met Pro Phe Leu Ile His Gln Trp Ala Arg Gly
                85                  90                  95

Gly Glu Trp Val Phe Gly Gly Pro Leu Cys Thr Ile Ile Thr Ser Leu
            100                 105                 110

Asp Thr Cys Asn Gln Phe Ala Cys Ser Ala Ile Met Thr Val Met Ser
        115                 120                 125

Val Asp Arg Tyr Phe Ala Leu Val Gln Pro Phe Arg Leu Thr Ser Trp
    130                 135                 140

Arg Thr Arg Tyr Lys Thr Ile Arg Ile Asn Leu Gly Leu Trp Ala Ala
145                 150                 155                 160

Ser Phe Ile Leu Ala Leu Pro Val Trp Ile Tyr Ser Lys Val Ile Lys
                165                 170                 175

Phe Lys Asp Gly Val Glu Ser Cys Ala Phe Asp Leu Thr Ser Pro Asp
            180                 185                 190

Asp Val Leu Trp Tyr Thr Leu Tyr Leu Thr Ile Thr Thr Phe Phe Phe
    195                 200                 205

Pro Leu Pro Leu Ile Leu Val Cys Tyr Ile Leu Ile Leu Cys Tyr Thr
210                 215                 220

Trp Glu Met Tyr Gln Gln Asn Lys Asp Ala Arg Cys Cys Asn Pro Ser
225                 230                 235                 240

Val Pro Lys Gln Arg Val Met Lys Leu Thr Lys Met Val Leu Val Leu
                245                 250                 255

Val Ala Val Phe Ile Leu Ser Ala Ala Pro Tyr His Val Ile Gln Leu
            260                 265                 270

Val Asn Leu Gln Met Glu Gln Pro Thr Leu Ala Phe Tyr Val Gly Tyr
    275                 280                 285

Tyr Leu Ser Ile Cys Leu Ser Tyr Ala Ser Ser Ile Asn Pro Phe
    290                 295                 300

Leu Tyr Ile Leu Leu Ser Gly Asn Phe Gln Lys Arg Leu Pro Gln Val
305                 310                 315                 320

Gln Arg Arg Val Thr Glu Lys Ser Thr Ile
                325                 330
```

```
<210> SEQ ID NO 18
<211> LENGTH: 330
<212> TYPE: PRT
<213> ORGANISM: artificial sequence
<220> FEATURE:
<223> OTHER INFORMATION: Cynomolgus macaque MCH2R/canine MCH2R
      C-terminal chimera B

<400> SEQUENCE: 18

Met Asn Pro Phe His Ser Ser Cys Trp Asn Thr Ser Ala Glu Leu Ser
1               5                   10                  15

Asn Lys Ser Trp Asn Lys Glu Phe Ala Tyr Gln Thr Ala Ser Val Val
            20                  25                  30

Asp Thr Val Ile Leu Pro Ser Met Ile Gly Ile Ile Cys Ser Thr Gly
        35                  40                  45

Leu Val Gly Asn Ile Leu Ile Val Phe Thr Ile Ile Arg Ser Arg Lys
50                  55                  60

Lys Thr Val Pro Asp Ile Tyr Ile Cys Asn Leu Ala Val Ala Asp Leu
65                  70                  75                  80

Val His Ile Val Gly Met Pro Phe Leu Ile His Gln Trp Ala Arg Gly
                85                  90                  95

Gly Glu Trp Val Phe Gly Gly Pro Leu Cys Thr Ile Ile Thr Ser Leu
            100                 105                 110

Asp Thr Cys Asn Gln Phe Ala Cys Ser Ala Ile Met Thr Val Met Ser
        115                 120                 125

Val Asp Arg Tyr Phe Ala Leu Val Gln Pro Phe Arg Leu Thr Ser Trp
130                 135                 140

Arg Thr Arg Tyr Lys Thr Ile Arg Ile Asn Leu Gly Leu Trp Ala Ala
145                 150                 155                 160

Ser Phe Ile Leu Ala Leu Pro Val Trp Ile Tyr Ser Lys Val Ile Lys
                165                 170                 175

Phe Lys Asp Gly Val Glu Ser Cys Ala Phe Asp Leu Thr Ser Pro Asp
            180                 185                 190

Asp Val Leu Trp Tyr Thr Leu Tyr Leu Thr Ile Thr Thr Phe Phe Phe
        195                 200                 205

Pro Leu Pro Leu Ile Leu Val Cys Tyr Ile Leu Ile Leu Cys Tyr Thr
210                 215                 220

Trp Glu Met Tyr Gln Gln Asn Lys Asp Ala Arg Cys Cys Asn Pro Ser
225                 230                 235                 240

Val Pro Lys Gln Arg Val Met Lys Leu Thr Lys Met Val Leu Val Leu
                245                 250                 255

Val Ala Val Phe Ile Leu Ser Ala Ala Pro Tyr His Val Ile Gln Leu
            260                 265                 270

Val Asn Leu Gln Met Glu Gln Pro Thr Leu Ala Phe Tyr Val Gly Tyr
        275                 280                 285

Tyr Leu Ser Ile Cys Leu Ser Tyr Ala Ser Ser Ile Asn Pro Phe
290                 295                 300

Leu Tyr Ile Leu Leu Ser Gly Asn Phe Arg Lys Arg Leu Pro Gln Val
305                 310                 315                 320

Gln Arg Arg Val Thr Glu Lys Ser Thr Ile
                325                 330

<210> SEQ ID NO 19
<211> LENGTH: 370
<212> TYPE: PRT
<213> ORGANISM: artificial sequence
```

```
<220> FEATURE:
<223> OTHER INFORMATION: Cynomolgus macaque MCH2R/human NPY1
      C-terminal chimera

<400> SEQUENCE: 19

Met Asn Pro Phe His Ser Ser Cys Trp Asn Thr Ser Ala Glu Leu Ser
1               5                   10                  15

Asn Lys Ser Trp Asn Lys Glu Phe Ala Tyr Gln Thr Ala Ser Val Val
            20                  25                  30

Asp Thr Val Ile Leu Pro Ser Met Ile Gly Ile Ile Cys Ser Thr Gly
            35                  40                  45

Leu Val Gly Asn Ile Leu Ile Val Phe Thr Ile Ile Arg Ser Arg Lys
50                  55                  60

Lys Thr Val Pro Asp Ile Tyr Ile Cys Asn Leu Ala Val Ala Asp Leu
65                  70                  75                  80

Val His Ile Val Gly Met Pro Phe Leu Ile His Gln Trp Ala Arg Gly
                85                  90                  95

Gly Glu Trp Val Phe Gly Gly Pro Leu Cys Thr Ile Ile Thr Ser Leu
            100                 105                 110

Asp Thr Cys Asn Gln Phe Ala Cys Ser Ala Ile Met Thr Val Met Ser
            115                 120                 125

Val Asp Arg Tyr Phe Ala Leu Val Gln Pro Phe Arg Leu Thr Ser Trp
130                 135                 140

Arg Thr Arg Tyr Lys Thr Ile Arg Ile Asn Leu Gly Leu Trp Ala Ala
145                 150                 155                 160

Ser Phe Ile Leu Ala Leu Pro Val Trp Ile Tyr Ser Lys Val Ile Lys
                165                 170                 175

Phe Lys Asp Gly Val Glu Ser Cys Ala Phe Asp Leu Thr Ser Pro Asp
            180                 185                 190

Asp Val Leu Trp Tyr Thr Leu Tyr Leu Thr Ile Thr Thr Phe Phe Phe
            195                 200                 205

Pro Leu Pro Leu Ile Leu Val Cys Tyr Ile Leu Ile Leu Cys Tyr Thr
210                 215                 220

Trp Glu Met Tyr Gln Gln Asn Lys Asp Ala Arg Cys Cys Asn Pro Ser
225                 230                 235                 240

Val Pro Lys Gln Arg Val Met Lys Leu Thr Lys Met Val Leu Val Leu
                245                 250                 255

Val Ala Val Phe Ile Leu Ser Ala Ala Pro Tyr His Val Ile Gln Leu
            260                 265                 270

Val Asn Leu Gln Met Glu Gln Pro Thr Leu Ala Phe Tyr Val Gly Tyr
            275                 280                 285

Tyr Leu Ser Ile Cys Leu Ser Tyr Ala Ser Ser Ile Asn Pro Phe
            290                 295                 300

Leu Tyr Ile Leu Leu Ser Gly Asn Phe Gln Lys Arg Leu Gln Phe Phe
305                 310                 315                 320

Phe Asn Phe Cys Asp Phe Arg Ser Arg Asp Asp Tyr Glu Thr Ile
                325                 330                 335

Ala Met Ser Thr Met His Thr Asp Val Ser Lys Thr Ser Leu Lys Gln
            340                 345                 350

Ala Ser Pro Val Ala Phe Lys Lys Ile Asn Asn Asn Asp Asp Asn Glu
            355                 360                 365

Lys Ile
370
```

-continued

<210> SEQ ID NO 20
<211> LENGTH: 385
<212> TYPE: PRT
<213> ORGANISM: artificial sequence
<220> FEATURE:
<223> OTHER INFORMATION: Cynomolgus macaque MCH2R/human beta-2
     adrenergic receptor C-terminal chimera

<400> SEQUENCE: 20

Met Asn Pro Phe His Ser Ser Cys Trp Asn Thr Ser Ala Glu Leu Ser
1               5                   10                  15

Asn Lys Ser Trp Asn Lys Glu Phe Ala Tyr Gln Thr Ala Ser Val Val
            20                  25                  30

Asp Thr Val Ile Leu Pro Ser Met Ile Gly Ile Ile Cys Ser Thr Gly
        35                  40                  45

Leu Val Gly Asn Ile Leu Ile Val Phe Thr Ile Ile Arg Ser Arg Lys
    50                  55                  60

Lys Thr Val Pro Asp Ile Tyr Ile Cys Asn Leu Ala Val Ala Asp Leu
65                  70                  75                  80

Val His Ile Val Gly Met Pro Phe Leu Ile His Gln Trp Ala Arg Gly
                85                  90                  95

Gly Glu Trp Val Phe Gly Gly Pro Leu Cys Thr Ile Ile Thr Ser Leu
            100                 105                 110

Asp Thr Cys Asn Gln Phe Ala Cys Ser Ala Ile Met Thr Val Met Ser
        115                 120                 125

Val Asp Arg Tyr Phe Ala Leu Val Gln Pro Phe Arg Leu Thr Ser Trp
    130                 135                 140

Arg Thr Arg Tyr Lys Thr Ile Arg Ile Asn Leu Gly Leu Trp Ala Ala
145                 150                 155                 160

Ser Phe Ile Leu Ala Leu Pro Val Trp Ile Tyr Ser Lys Val Ile Lys
                165                 170                 175

Phe Lys Asp Gly Val Glu Ser Cys Ala Phe Asp Leu Thr Ser Pro Asp
            180                 185                 190

Asp Val Leu Trp Tyr Thr Leu Tyr Leu Thr Ile Thr Thr Phe Phe Phe
        195                 200                 205

Pro Leu Pro Leu Ile Leu Val Cys Tyr Ile Leu Ile Leu Cys Tyr Thr
    210                 215                 220

Trp Glu Met Tyr Gln Gln Asn Lys Asp Ala Arg Cys Cys Asn Pro Ser
225                 230                 235                 240

Val Pro Lys Gln Arg Val Met Lys Leu Thr Lys Met Val Leu Val Leu
                245                 250                 255

Val Ala Val Phe Ile Leu Ser Ala Ala Pro Tyr His Val Ile Gln Leu
            260                 265                 270

Val Asn Leu Gln Met Glu Gln Pro Thr Leu Ala Phe Tyr Val Gly Tyr
        275                 280                 285

Tyr Leu Ser Ile Cys Leu Ser Tyr Ala Ser Ser Ile Asn Pro Phe
    290                 295                 300

Leu Tyr Ile Leu Leu Ser Gly Asn Phe Gln Lys Arg Ser Ser Leu Lys
305                 310                 315                 320

Ala Tyr Gly Asn Gly Tyr Ser Ser Asn Gly Asn Thr Gly Glu Gln Ser
                325                 330                 335

Gly Tyr His Val Glu Gln Glu Lys Glu Asn Lys Leu Leu Cys Glu Asp
            340                 345                 350

Leu Pro Gly Thr Glu Asp Phe Val Gly His Gln Gly Thr Val Pro Ser
        355                 360                 365

```
Asp Asn Ile Asp Ser Gln Gly Arg Asn Cys Ser Thr Asn Asp Ser Leu
        370                 375                 380

Leu
385

<210> SEQ ID NO 21
<211> LENGTH: 346
<212> TYPE: PRT
<213> ORGANISM: artificial sequence
<220> FEATURE:
<223> OTHER INFORMATION: Cynomolgus macaque MCH2R/MCH1R N-terminal
      chimera A

<400> SEQUENCE: 21

Met Asp Leu Glu Ala Ser Leu Leu Pro Thr Gly Pro Asn Thr Ser Asn
 1               5                  10                  15

Thr Ser Asp Gly Pro Asp Asn Leu Thr Ser Ala Gly Ser Pro Pro Arg
            20                  25                  30

Ser Gly Ala Ser Val Val Asp Val Ile Leu Pro Ser Met Ile Gly
        35                  40                  45

Ile Ile Cys Ser Thr Gly Leu Val Gly Asn Ile Leu Ile Val Phe Thr
 50                  55                  60

Ile Ile Arg Ser Arg Lys Lys Thr Val Pro Asp Ile Tyr Ile Cys Asn
65                  70                  75                  80

Leu Ala Val Ala Asp Leu Val His Ile Val Gly Met Pro Phe Leu Ile
                85                  90                  95

His Gln Trp Ala Arg Gly Gly Glu Trp Val Phe Gly Gly Pro Leu Cys
            100                 105                 110

Thr Ile Ile Thr Ser Leu Asp Thr Cys Asn Gln Phe Ala Cys Ser Ala
        115                 120                 125

Ile Met Thr Val Met Ser Val Asp Arg Tyr Phe Ala Leu Val Gln Pro
130                 135                 140

Phe Arg Leu Thr Ser Trp Arg Thr Arg Tyr Lys Thr Ile Arg Ile Asn
145                 150                 155                 160

Leu Gly Leu Trp Ala Ala Ser Phe Ile Leu Ala Leu Pro Val Trp Ile
                165                 170                 175

Tyr Ser Lys Val Ile Lys Phe Lys Asp Gly Val Glu Ser Cys Ala Phe
            180                 185                 190

Asp Leu Thr Ser Pro Asp Asp Val Leu Trp Tyr Thr Leu Tyr Leu Thr
        195                 200                 205

Ile Thr Thr Phe Phe Pro Leu Pro Leu Ile Leu Val Cys Tyr Ile
210                 215                 220

Leu Ile Leu Cys Tyr Thr Trp Glu Met Tyr Gln Gln Asn Lys Asp Ala
225                 230                 235                 240

Arg Cys Cys Asn Pro Ser Val Pro Lys Gln Arg Val Met Lys Leu Thr
                245                 250                 255

Lys Met Val Leu Val Leu Val Ala Val Phe Ile Leu Ser Ala Ala Pro
            260                 265                 270

Tyr His Val Ile Gln Leu Val Asn Leu Gln Met Glu Gln Pro Thr Leu
        275                 280                 285

Ala Phe Tyr Val Gly Tyr Tyr Leu Ser Ile Cys Leu Ser Tyr Ala Ser
290                 295                 300

Ser Ser Ile Asn Pro Phe Leu Tyr Ile Leu Leu Ser Gly Asn Phe Gln
305                 310                 315                 320

Lys Arg Leu Pro Gln Ile Gln Arg Arg Val Thr Asp Lys Glu Ile Lys
                325                 330                 335
```

Asn Met Gly Asn Thr Leu Lys Ser His Phe
            340                 345

<210> SEQ ID NO 22
<211> LENGTH: 340
<212> TYPE: PRT
<213> ORGANISM: artificial sequence
<220> FEATURE:
<223> OTHER INFORMATION: Cynomolgus macaque MCH2R/canine MCH2R
      N-terminal chimera A

<400> SEQUENCE: 22

Met Tyr Ser Leu His Ser Ser Cys Trp Asn Thr Ser Ala Glu Pro Leu
1               5                   10                  15

Asn Lys Ser Cys Asn Lys Glu Phe Ala Tyr His Thr Ala Ser Val Val
            20                  25                  30

Asp Thr Val Ile Leu Pro Ser Met Ile Gly Ile Ile Cys Ser Thr Gly
        35                  40                  45

Leu Val Gly Asn Ile Leu Ile Val Phe Thr Ile Ile Arg Ser Arg Lys
    50                  55                  60

Lys Thr Val Pro Asp Ile Tyr Ile Cys Asn Leu Ala Val Ala Asp Leu
65                  70                  75                  80

Val His Ile Val Gly Met Pro Phe Leu Ile His Gln Trp Ala Arg Gly
                85                  90                  95

Gly Glu Trp Val Phe Gly Gly Pro Leu Cys Thr Ile Ile Thr Ser Leu
            100                 105                 110

Asp Thr Cys Asn Gln Phe Ala Cys Ser Ala Ile Met Thr Val Met Ser
        115                 120                 125

Val Asp Arg Tyr Phe Ala Leu Val Gln Pro Phe Arg Leu Thr Ser Trp
    130                 135                 140

Arg Thr Arg Tyr Lys Thr Ile Arg Ile Asn Leu Gly Leu Trp Ala Ala
145                 150                 155                 160

Ser Phe Ile Leu Ala Leu Pro Val Trp Ile Tyr Ser Lys Val Ile Lys
                165                 170                 175

Phe Lys Asp Gly Val Glu Ser Cys Ala Phe Asp Leu Thr Ser Pro Asp
            180                 185                 190

Asp Val Leu Trp Tyr Thr Leu Tyr Leu Thr Ile Thr Thr Phe Phe Phe
        195                 200                 205

Pro Leu Pro Leu Ile Leu Val Cys Tyr Ile Leu Ile Leu Cys Tyr Thr
    210                 215                 220

Trp Glu Met Tyr Gln Gln Asn Lys Asp Ala Arg Cys Cys Asn Pro Ser
225                 230                 235                 240

Val Pro Lys Gln Arg Val Met Lys Leu Thr Lys Met Val Leu Val Leu
                245                 250                 255

Val Ala Val Phe Ile Leu Ser Ala Ala Pro Tyr His Val Ile Gln Leu
            260                 265                 270

Val Asn Leu Gln Met Glu Gln Pro Thr Leu Ala Phe Tyr Val Gly Tyr
        275                 280                 285

Tyr Leu Ser Ile Cys Leu Ser Tyr Ala Ser Ser Ile Asn Pro Phe
    290                 295                 300

Leu Tyr Ile Leu Leu Ser Gly Asn Phe Gln Lys Arg Leu Pro Gln Ile
305                 310                 315                 320

Gln Arg Arg Val Thr Asp Lys Glu Ile Lys Asn Met Gly Asn Thr Leu
                325                 330                 335

Lys Ser His Phe

<210> SEQ ID NO 23
<211> LENGTH: 346
<212> TYPE: PRT
<213> ORGANISM: artificial sequence
<220> FEATURE:
<223> OTHER INFORMATION: Cynomolgus macaque MCH2R/MCH1R N-terminal chimera B

<400> SEQUENCE: 23

```
Met Asp Leu Glu Ala Ser Leu Leu Pro Thr Gly Pro Asn Thr Ser Asn
1               5                   10                  15

Thr Ser Asp Gly Pro Asp Asn Leu Thr Ser Ala Gly Ser Pro Pro Arg
            20                  25                  30

Ser Gly Ser Val Ser Val Asp Thr Val Ile Leu Pro Ser Met Ile Gly
        35                  40                  45

Ile Ile Cys Ser Thr Gly Leu Val Gly Asn Ile Leu Ile Val Phe Thr
50                  55                  60

Ile Ile Arg Ser Arg Lys Lys Thr Val Pro Asp Ile Tyr Ile Cys Asn
65                  70                  75                  80

Leu Ala Val Ala Asp Leu Val His Ile Val Gly Met Pro Phe Leu Ile
                85                  90                  95

His Gln Trp Ala Arg Gly Gly Glu Trp Val Phe Gly Gly Pro Leu Cys
            100                 105                 110

Thr Ile Ile Thr Ser Leu Asp Thr Cys Asn Gln Phe Ala Cys Ser Ala
        115                 120                 125

Ile Met Thr Val Met Ser Val Asp Arg Tyr Phe Ala Leu Val Gln Pro
130                 135                 140

Phe Arg Leu Thr Ser Trp Arg Thr Arg Tyr Lys Thr Ile Arg Ile Asn
145                 150                 155                 160

Leu Gly Leu Trp Ala Ala Ser Phe Ile Leu Ala Leu Pro Val Trp Ile
                165                 170                 175

Tyr Ser Lys Val Ile Lys Phe Lys Asp Gly Val Glu Ser Cys Ala Phe
            180                 185                 190

Asp Leu Thr Ser Pro Asp Asp Val Leu Trp Tyr Thr Leu Tyr Leu Thr
        195                 200                 205

Ile Thr Thr Phe Phe Pro Leu Pro Leu Ile Leu Val Cys Tyr Ile
210                 215                 220

Leu Ile Leu Cys Tyr Thr Trp Glu Met Tyr Gln Gln Asn Lys Asp Ala
225                 230                 235                 240

Arg Cys Cys Asn Pro Ser Val Pro Lys Gln Arg Val Met Lys Leu Thr
                245                 250                 255

Lys Met Val Leu Val Leu Val Ala Val Phe Ile Leu Ser Ala Ala Pro
            260                 265                 270

Tyr His Val Ile Gln Leu Val Asn Leu Gln Met Glu Gln Pro Thr Leu
        275                 280                 285

Ala Phe Tyr Val Gly Tyr Tyr Leu Ser Ile Cys Leu Ser Tyr Ala Ser
290                 295                 300

Ser Ser Ile Asn Pro Phe Leu Tyr Ile Leu Leu Ser Gly Asn Phe Gln
305                 310                 315                 320

Lys Arg Leu Pro Gln Ile Gln Arg Arg Val Thr Asp Lys Glu Ile Lys
                325                 330                 335

Asn Met Gly Asn Thr Leu Lys Ser His Phe
            340                 345
```

<210> SEQ ID NO 24
<211> LENGTH: 340
<212> TYPE: PRT
<213> ORGANISM: artificial sequence
<220> FEATURE:
<223> OTHER INFORMATION: Cynomolgus macaque MCH2R/canine MCH2R
    N-terminal chimera B

<400> SEQUENCE: 24

Met Tyr Ser Leu His Ser Ser Cys Trp Asn Thr Ser Ala Glu Pro Leu
1               5                   10                  15

Asn Lys Ser Cys Asn Lys Glu Phe Ala Tyr His Thr Leu Ser Ile Val
            20                  25                  30

Asp Thr Val Ile Leu Pro Ser Met Ile Gly Ile Ile Cys Ser Thr Gly
        35                  40                  45

Leu Val Gly Asn Ile Leu Ile Val Phe Thr Ile Ile Arg Ser Arg Lys
    50                  55                  60

Lys Thr Val Pro Asp Ile Tyr Ile Cys Asn Leu Ala Val Ala Asp Leu
65                  70                  75                  80

Val His Ile Val Gly Met Pro Phe Leu Ile His Gln Trp Ala Arg Gly
                85                  90                  95

Gly Glu Trp Val Phe Gly Gly Pro Leu Cys Thr Ile Ile Thr Ser Leu
            100                 105                 110

Asp Thr Cys Asn Gln Phe Ala Cys Ser Ala Ile Met Thr Val Met Ser
        115                 120                 125

Val Asp Arg Tyr Phe Ala Leu Val Gln Pro Phe Arg Leu Thr Ser Trp
    130                 135                 140

Arg Thr Arg Tyr Lys Thr Ile Arg Ile Asn Leu Gly Leu Trp Ala Ala
145                 150                 155                 160

Ser Phe Ile Leu Ala Leu Pro Val Trp Ile Tyr Ser Lys Val Ile Lys
                165                 170                 175

Phe Lys Asp Gly Val Glu Ser Cys Ala Phe Asp Leu Thr Ser Pro Asp
            180                 185                 190

Asp Val Leu Trp Tyr Thr Leu Tyr Leu Thr Ile Thr Thr Phe Phe Phe
        195                 200                 205

Pro Leu Pro Leu Ile Leu Val Cys Tyr Ile Leu Ile Leu Cys Tyr Thr
    210                 215                 220

Trp Glu Met Tyr Gln Gln Asn Lys Asp Ala Arg Cys Cys Asn Pro Ser
225                 230                 235                 240

Val Pro Lys Gln Arg Val Met Lys Leu Thr Lys Met Val Leu Val Leu
                245                 250                 255

Val Ala Val Phe Ile Leu Ser Ala Ala Pro Tyr His Val Ile Gln Leu
            260                 265                 270

Val Asn Leu Gln Met Glu Gln Pro Thr Leu Ala Phe Tyr Val Gly Tyr
        275                 280                 285

Tyr Leu Ser Ile Cys Leu Ser Tyr Ala Ser Ser Ile Asn Pro Phe
    290                 295                 300

Leu Tyr Ile Leu Leu Ser Gly Asn Phe Gln Lys Arg Leu Pro Gln Ile
305                 310                 315                 320

Gln Arg Arg Val Thr Asp Lys Glu Ile Lys Asn Met Gly Asn Thr Leu
                325                 330                 335

Lys Ser His Phe
            340

<210> SEQ ID NO 25

<211> LENGTH: 334
<212> TYPE: PRT
<213> ORGANISM: artificial sequence
<220> FEATURE:
<223> OTHER INFORMATION: Cynomolgus macaque MCH2R/MCH1R IC3 loop chimera

<400> SEQUENCE: 25

```
Met Asn Pro Phe His Ser Ser Cys Trp Asn Thr Ser Ala Glu Leu Ser
1               5                   10                  15

Asn Lys Ser Trp Asn Lys Glu Phe Ala Tyr Gln Thr Ala Ser Val Val
            20                  25                  30

Asp Thr Val Ile Leu Pro Ser Met Ile Gly Ile Ile Cys Ser Thr Gly
        35                  40                  45

Leu Val Gly Asn Ile Leu Ile Val Phe Thr Ile Arg Ser Arg Lys
    50                  55                  60

Lys Thr Val Pro Asp Ile Tyr Ile Cys Asn Leu Ala Val Ala Asp Leu
65                  70                  75                  80

Val His Ile Val Gly Met Pro Phe Leu Ile His Gln Trp Ala Arg Gly
                85                  90                  95

Gly Glu Trp Val Phe Gly Gly Pro Leu Cys Thr Ile Ile Thr Ser Leu
            100                 105                 110

Asp Thr Cys Asn Gln Phe Ala Cys Ser Ala Ile Met Thr Val Met Ser
        115                 120                 125

Val Asp Arg Tyr Phe Ala Leu Val Gln Pro Phe Arg Leu Thr Ser Trp
    130                 135                 140

Arg Thr Arg Tyr Lys Thr Ile Arg Ile Asn Leu Gly Leu Trp Ala Ala
145                 150                 155                 160

Ser Phe Ile Leu Ala Leu Pro Val Trp Ile Tyr Ser Lys Val Ile Lys
                165                 170                 175

Phe Lys Asp Gly Val Glu Ser Cys Ala Phe Asp Leu Thr Ser Pro Asp
            180                 185                 190

Asp Val Leu Trp Tyr Thr Leu Tyr Leu Thr Ile Thr Thr Phe Phe Phe
        195                 200                 205

Pro Leu Pro Leu Ile Leu Val Cys Tyr Ile Leu Ile Leu Cys Tyr Met
    210                 215                 220

Thr Ser Ser Val Ala Pro Ala Ser Gln Arg Ser Ile Arg Leu Arg Thr
225                 230                 235                 240

Met Lys Leu Thr Lys Met Val Leu Val Leu Ala Val Phe Ile Leu
                245                 250                 255

Ser Ala Ala Pro Tyr His Val Ile Gln Leu Val Asn Leu Gln Met Glu
            260                 265                 270

Gln Pro Thr Leu Ala Phe Tyr Val Gly Tyr Tyr Leu Ser Ile Cys Leu
        275                 280                 285

Ser Tyr Ala Ser Ser Ser Ile Asn Pro Phe Leu Tyr Ile Leu Leu Ser
    290                 295                 300

Gly Asn Phe Gln Lys Arg Leu Pro Gln Ile Gln Arg Arg Val Thr Asp
305                 310                 315                 320

Lys Glu Ile Lys Asn Met Gly Asn Thr Leu Lys Ser His Phe
                325                 330
```

<210> SEQ ID NO 26
<211> LENGTH: 340
<212> TYPE: PRT
<213> ORGANISM: artificial sequence
<220> FEATURE:
<223> OTHER INFORMATION: Cynomolgus macaque MCH2R/canine MCH2R IC3
      loop chimera

<400> SEQUENCE: 26

```
Met Asn Pro Phe His Ser Ser Cys Trp Asn Thr Ser Ala Glu Leu Ser
1               5                   10                  15
Asn Lys Ser Trp Asn Lys Glu Phe Ala Tyr Gln Thr Ala Ser Val Val
            20                  25                  30
Asp Thr Val Ile Leu Pro Ser Met Ile Gly Ile Ile Cys Ser Thr Gly
        35                  40                  45
Leu Val Gly Asn Ile Leu Ile Val Phe Thr Ile Ile Arg Ser Arg Lys
    50                  55                  60
Lys Thr Val Pro Asp Ile Tyr Ile Cys Asn Leu Ala Val Ala Asp Leu
65                  70                  75                  80
Val His Ile Val Gly Met Pro Phe Leu Ile His Gln Trp Ala Arg Gly
                85                  90                  95
Gly Glu Trp Val Phe Gly Gly Pro Leu Cys Thr Ile Ile Thr Ser Leu
            100                 105                 110
Asp Thr Cys Asn Gln Phe Ala Cys Ser Ala Ile Met Thr Val Met Ser
        115                 120                 125
Val Asp Arg Tyr Phe Ala Leu Val Gln Pro Phe Arg Leu Thr Ser Trp
    130                 135                 140
Arg Thr Arg Tyr Lys Thr Ile Arg Ile Asn Leu Gly Leu Trp Ala Ala
145                 150                 155                 160
Ser Phe Ile Leu Ala Leu Pro Val Trp Ile Tyr Ser Lys Val Ile Lys
                165                 170                 175
Phe Lys Asp Gly Val Glu Ser Cys Ala Phe Asp Leu Thr Ser Pro Asp
            180                 185                 190
Asp Val Leu Trp Tyr Thr Leu Tyr Leu Thr Ile Thr Thr Phe Phe Phe
        195                 200                 205
Pro Leu Pro Leu Ile Leu Val Cys Tyr Ile Leu Ile Leu Cys Tyr Thr
    210                 215                 220
Trp Glu Met Tyr Gln Gln Asn Lys Asp Ala Arg Cys Tyr Asn Pro Ser
225                 230                 235                 240
Val Pro Lys Glu Arg Val Met Lys Leu Thr Lys Met Val Leu Val Leu
                245                 250                 255
Val Ala Val Phe Ile Leu Ser Ala Ala Pro Tyr His Val Ile Gln Leu
            260                 265                 270
Val Asn Leu Gln Met Glu Gln Pro Thr Leu Ala Phe Tyr Val Gly Tyr
        275                 280                 285
Tyr Leu Ser Ile Cys Leu Ser Tyr Ala Ser Ser Ser Ile Asn Pro Phe
    290                 295                 300
Leu Tyr Ile Leu Leu Ser Gly Asn Phe Gln Lys Arg Leu Pro Gln Ile
305                 310                 315                 320
Gln Arg Arg Val Thr Asp Lys Glu Ile Lys Asn Met Gly Asn Thr Leu
                325                 330                 335
Lys Ser His Phe
            340
```

<210> SEQ ID NO 27
<211> LENGTH: 338
<212> TYPE: PRT
<213> ORGANISM: artificial sequence
<220> FEATURE:
<223> OTHER INFORMATION: Cynomolgus macaque MCH2R/human NPY1 IC3 loop chimera

<400> SEQUENCE: 27

```
Met Asn Pro Phe His Ser Ser Cys Trp Asn Thr Ser Ala Glu Leu Ser
1               5                   10                  15

Asn Lys Ser Trp Asn Lys Glu Phe Ala Tyr Gln Thr Ala Ser Val Val
            20                  25                  30

Asp Thr Val Ile Leu Pro Ser Met Ile Gly Ile Ile Cys Ser Thr Gly
            35                  40                  45

Leu Val Gly Asn Ile Leu Ile Val Phe Thr Ile Ile Arg Ser Arg Lys
        50                  55                  60

Lys Thr Val Pro Asp Ile Tyr Ile Cys Asn Leu Ala Val Ala Asp Leu
65                  70                  75                  80

Val His Ile Val Gly Met Pro Phe Leu Ile His Gln Trp Ala Arg Gly
                85                  90                  95

Gly Glu Trp Val Phe Gly Gly Pro Leu Cys Thr Ile Ile Thr Ser Leu
                100                 105                 110

Asp Thr Cys Asn Gln Phe Ala Cys Ser Ala Ile Met Thr Val Met Ser
            115                 120                 125

Val Asp Arg Tyr Phe Ala Leu Val Gln Pro Phe Arg Leu Thr Ser Trp
130                 135                 140

Arg Thr Arg Tyr Lys Thr Ile Arg Ile Asn Leu Gly Leu Trp Ala Ala
145                 150                 155                 160

Ser Phe Ile Leu Ala Leu Pro Val Trp Ile Tyr Ser Lys Val Ile Lys
                165                 170                 175

Phe Lys Asp Gly Val Glu Ser Cys Ala Phe Asp Leu Thr Ser Pro Asp
            180                 185                 190

Asp Val Leu Trp Tyr Thr Leu Tyr Leu Thr Ile Thr Thr Phe Phe Phe
            195                 200                 205

Pro Leu Pro Leu Ile Leu Val Cys Tyr Ile Leu Ile Leu Cys Tyr Leu
        210                 215                 220

Lys Arg Arg Asn Asn Met Met Asp Lys Met Arg Asp Asn Lys Tyr Arg
225                 230                 235                 240

Ser Ser Glu Thr Met Lys Leu Thr Lys Met Val Leu Val Leu Val Ala
            245                 250                 255

Val Phe Ile Leu Ser Ala Ala Pro Tyr His Val Ile Gln Leu Val Asn
                260                 265                 270

Leu Gln Met Glu Gln Pro Thr Leu Ala Phe Tyr Val Gly Tyr Tyr Leu
            275                 280                 285

Ser Ile Cys Leu Ser Tyr Ala Ser Ser Ser Ile Asn Pro Phe Leu Tyr
            290                 295                 300

Ile Leu Leu Ser Gly Asn Phe Gln Lys Arg Leu Pro Gln Ile Gln Arg
305                 310                 315                 320

Arg Val Thr Asp Lys Glu Ile Lys Asn Met Gly Asn Thr Leu Lys Ser
                325                 330                 335

His Phe
```

<210> SEQ ID NO 28
<211> LENGTH: 360
<212> TYPE: PRT
<213> ORGANISM: artificial sequence
<220> FEATURE:
<223> OTHER INFORMATION: Cynomolgus macaque MCH2R/human beta-2 adrenergic receptor IC3 loop chimera

<400> SEQUENCE: 28

```
Met Asn Pro Phe His Ser Ser Cys Trp Asn Thr Ser Ala Glu Leu Ser
1               5                   10                  15
```

```
Asn Lys Ser Trp Asn Lys Glu Phe Ala Tyr Gln Thr Ala Ser Val Val
            20                  25                  30

Asp Thr Val Ile Leu Pro Ser Met Ile Gly Ile Ile Cys Ser Thr Gly
            35                  40                  45

Leu Val Gly Asn Ile Leu Ile Val Phe Thr Ile Ile Arg Ser Arg Lys
        50                  55                  60

Lys Thr Val Pro Asp Ile Tyr Ile Cys Asn Leu Ala Val Ala Asp Leu
65                  70                  75                  80

Val His Ile Val Gly Met Pro Phe Leu Ile His Gln Trp Ala Arg Gly
                85                  90                  95

Gly Glu Trp Val Phe Gly Gly Pro Leu Cys Thr Ile Thr Ser Leu
                100                 105                 110

Asp Thr Cys Asn Gln Phe Ala Cys Ser Ala Ile Met Thr Val Met Ser
            115                 120                 125

Val Asp Arg Tyr Phe Ala Leu Val Gln Pro Phe Arg Leu Thr Ser Trp
        130                 135                 140

Arg Thr Arg Tyr Lys Thr Ile Arg Ile Asn Leu Gly Leu Trp Ala Ala
145                 150                 155                 160

Ser Phe Ile Leu Ala Leu Pro Val Trp Ile Tyr Ser Lys Val Ile Lys
                165                 170                 175

Phe Lys Asp Gly Val Glu Ser Cys Ala Phe Asp Leu Thr Ser Pro Asp
            180                 185                 190

Asp Val Leu Trp Tyr Thr Leu Tyr Leu Thr Ile Thr Thr Phe Phe Phe
        195                 200                 205

Pro Leu Pro Leu Ile Leu Val Cys Tyr Ile Leu Ile Leu Cys Tyr Ala
    210                 215                 220

Lys Arg Gln Leu Gln Lys Ile Asp Lys Ser Glu Gly Arg Phe His Val
225                 230                 235                 240

Gln Asn Leu Ser Gln Val Glu Gln Asp Gly Arg Thr Gly His Gly Leu
                245                 250                 255

Arg Arg Ser Ser Lys Phe Cys Leu Lys Glu Met Lys Leu Thr Lys Met
            260                 265                 270

Val Leu Val Leu Val Ala Val Phe Ile Leu Ser Ala Ala Pro Tyr His
        275                 280                 285

Val Ile Gln Leu Val Asn Leu Gln Met Glu Gln Pro Thr Leu Ala Phe
    290                 295                 300

Tyr Val Gly Tyr Tyr Leu Ser Ile Cys Leu Ser Tyr Ala Ser Ser Ser
305                 310                 315                 320

Ile Asn Pro Phe Leu Tyr Ile Leu Leu Ser Gly Asn Phe Gln Lys Arg
                325                 330                 335

Leu Pro Gln Ile Gln Arg Arg Val Thr Asp Lys Glu Ile Lys Asn Met
            340                 345                 350

Gly Asn Thr Leu Lys Ser His Phe
            355                 360

<210> SEQ ID NO 29
<211> LENGTH: 340
<212> TYPE: PRT
<213> ORGANISM: Homo sapiens

<400> SEQUENCE: 29

Met Asn Pro Phe His Ala Ser Cys Trp Asn Thr Ser Ala Glu Leu Leu
1               5                   10                  15

Asn Lys Ser Trp Asn Lys Glu Phe Ala Tyr Gln Thr Ala Ser Val Val
```

```
                 20                  25                  30
Asp Thr Val Ile Leu Pro Ser Met Ile Gly Ile Cys Ser Thr Gly
             35                  40                  45
Leu Val Gly Asn Ile Leu Ile Val Phe Thr Ile Ile Arg Ser Arg Lys
 50                  55                  60
Lys Thr Val Pro Asp Ile Tyr Ile Cys Asn Leu Ala Val Ala Asp Leu
 65                  70                  75                  80
Val His Ile Val Gly Met Pro Phe Leu Ile His Gln Trp Ala Arg Gly
             85                  90                  95
Gly Glu Trp Val Phe Gly Gly Pro Leu Cys Thr Ile Thr Ser Leu
             100                 105                 110
Asp Thr Cys Asn Gln Phe Ala Cys Ser Ala Ile Met Thr Val Met Ser
             115                 120                 125
Val Asp Arg Tyr Phe Ala Leu Val Gln Pro Phe Arg Leu Thr Arg Trp
 130                 135                 140
Arg Thr Arg Tyr Lys Thr Ile Arg Ile Asn Leu Gly Leu Trp Ala Ala
 145                 150                 155                 160
Ser Phe Ile Leu Ala Leu Pro Val Trp Val Tyr Ser Lys Val Ile Lys
             165                 170                 175
Phe Lys Asp Gly Val Glu Ser Cys Ala Phe Asp Leu Thr Ser Pro Asp
             180                 185                 190
Asp Val Leu Trp Tyr Thr Leu Tyr Leu Thr Ile Thr Thr Phe Phe Phe
 195                 200                 205
Pro Leu Pro Leu Ile Leu Val Cys Tyr Ile Leu Ile Leu Cys Tyr Thr
 210                 215                 220
Trp Glu Met Tyr Gln Gln Asn Lys Asp Ala Arg Cys Cys Asn Pro Ser
225                 230                 235                 240
Val Pro Lys Gln Arg Val Met Lys Leu Thr Lys Met Val Leu Val Leu
             245                 250                 255
Val Val Val Phe Ile Leu Ser Ala Ala Pro Tyr His Val Ile Gln Leu
             260                 265                 270
Val Asn Leu Gln Met Glu Gln Pro Thr Leu Ala Phe Tyr Val Gly Tyr
 275                 280                 285
Tyr Leu Ser Ile Cys Leu Ser Tyr Ala Ser Ser Ile Asn Pro Phe
 290                 295                 300
Leu Tyr Ile Leu Leu Ser Gly Asn Phe Gln Lys Arg Leu Pro Gln Ile
305                 310                 315                 320
Gln Arg Arg Ala Thr Glu Lys Glu Ile Asn Asn Met Gly Asn Thr Leu
             325                 330                 335
Lys Ser His Phe
             340

<210> SEQ ID NO 30
<211> LENGTH: 353
<212> TYPE: PRT
<213> ORGANISM: Macaca fascicularis

<400> SEQUENCE: 30

Met Asp Leu Glu Ala Ser Leu Leu Pro Thr Gly Pro Asn Thr Ser Asn
 1               5                  10                  15
Thr Ser Asp Gly Pro Asp Asn Leu Thr Ser Ala Gly Ser Pro Pro Arg
             20                  25                  30
Ser Gly Ser Val Ser Tyr Ile Asn Ile Ile Met Pro Ser Val Phe Gly
             35                  40                  45
```

```
Thr Ile Cys Leu Leu Gly Ile Ile Gly Asn Ser Met Val Ile Phe Ala
 50                  55                  60

Val Val Lys Lys Ser Lys Leu His Trp Cys Asn Asn Val Pro Asp Ile
 65                  70                  75                  80

Phe Ile Ile Asn Leu Ser Val Val Asp Leu Leu Phe Leu Leu Gly Met
                 85                  90                  95

Pro Phe Met Ile His Gln Leu Met Gly Asn Gly Val Trp His Phe Gly
            100                 105                 110

Glu Thr Met Cys Thr Leu Ile Thr Ala Met Asp Ala Asn Ser Gln Phe
            115                 120                 125

Thr Ser Thr Tyr Ile Leu Thr Ala Met Ala Ile Asp Arg Tyr Leu Ala
130                 135                 140

Thr Val His Pro Ile Ser Ser Thr Lys Phe Arg Lys Pro Ser Val Ala
145                 150                 155                 160

Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
                180                 185                 190

Gly Cys Gly Ile Arg Leu Pro Asn Pro Asp Thr Asp Leu Tyr Trp Phe
            195                 200                 205

Thr Leu Tyr Gln Phe Phe Leu Ala Phe Ala Leu Pro Phe Val Val Ile
210                 215                 220

Thr Ala Ala Tyr Val Arg Ile Leu Gln Arg Met Thr Ser Ser Val Ala
225                 230                 235                 240

Pro Ala Ser Gln Arg Ser Ile Arg Leu Arg Thr Lys Arg Val Thr Arg
                245                 250                 255

Thr Ala Ile Ala Ile Cys Leu Val Phe Phe Val Cys Trp Ala Pro Tyr
            260                 265                 270

Tyr Val Leu Gln Leu Thr Gln Leu Ser Ile Ser Arg Pro Thr Leu Thr
            275                 280                 285

Phe Val Tyr Leu Tyr Asn Ala Ala Ile Ser Leu Gly Tyr Ala Asn Ser
290                 295                 300

Cys Leu Asn Pro Phe Val Tyr Ile Val Leu Cys Glu Thr Phe Arg Lys
305                 310                 315                 320

Arg Leu Val Leu Ser Val Lys Pro Ala Ala Gln Gly Gln Leu Arg Ala
                325                 330                 335

Val Ser Asn Ala Gln Thr Ala Asp Glu Glu Arg Thr Glu Ser Lys Gly
            340                 345                 350

Thr

<210> SEQ ID NO 31
<211> LENGTH: 384
<212> TYPE: PRT
<213> ORGANISM: Homo sapiens

<400> SEQUENCE: 31

Met Asn Ser Thr Leu Phe Ser Gln Val Glu Asn His Ser Val His Ser
 1               5                  10                  15

Asn Phe Ser Glu Lys Asn Ala Gln Leu Leu Ala Phe Glu Asn Asp Asp
             20                  25                  30

Cys His Leu Pro Leu Ala Met Ile Phe Thr Leu Ala Leu Ala Tyr Gly
         35                  40                  45

Ala Val Ile Ile Leu Gly Val Ser Gly Asn Leu Ala Leu Ile Ile Ile
 50                  55                  60
```

```
Ile Leu Lys Gln Lys Glu Met Arg Asn Val Thr Asn Ile Leu Ile Val
 65                  70                  75                  80

Asn Leu Ser Phe Ser Asp Leu Leu Val Ala Ile Met Cys Leu Pro Phe
                 85                  90                  95

Thr Phe Val Tyr Thr Leu Met Asp His Trp Val Phe Gly Glu Ala Met
            100                 105                 110

Cys Lys Leu Asn Pro Phe Val Gln Cys Val Ser Ile Thr Val Ser Ile
        115                 120                 125

Phe Ser Leu Val Leu Ile Ala Val Glu Arg His Gln Leu Ile Ile Asn
130                 135                 140

Pro Arg Gly Trp Arg Pro Asn Asn Arg His Ala Tyr Val Gly Ile Ala
145                 150                 155                 160

Val Ile Trp Val Leu Ala Val Ala Ser Ser Leu Pro Phe Leu Ile Tyr
                165                 170                 175

Gln Val Met Thr Asp Glu Pro Phe Gln Asn Val Thr Leu Asp Ala Tyr
            180                 185                 190

Lys Asp Lys Tyr Val Cys Phe Asp Gln Phe Pro Ser Asp Ser His Arg
        195                 200                 205

Leu Ser Tyr Thr Thr Leu Leu Leu Val Leu Gln Tyr Phe Gly Pro Leu
210                 215                 220

Cys Phe Ile Phe Ile Cys Tyr Phe Lys Ile Tyr Ile Arg Leu Lys Arg
225                 230                 235                 240

Arg Asn Asn Met Met Asp Lys Met Arg Asp Asn Lys Tyr Arg Ser Ser
                245                 250                 255

Glu Thr Lys Arg Ile Asn Ile Met Leu Leu Ser Ile Val Val Ala Phe
            260                 265                 270

Ala Val Cys Trp Leu Pro Leu Thr Ile Phe Asn Thr Val Phe Asp Trp
        275                 280                 285

Asn His Gln Ile Ile Ala Thr Cys Asn His Asn Leu Leu Phe Leu Leu
290                 295                 300

Cys His Leu Thr Ala Met Ile Ser Thr Cys Val Asn Pro Ile Phe Tyr
305                 310                 315                 320

Gly Phe Leu Asn Lys Asn Phe Gln Arg Asp Leu Gln Phe Phe Phe Asn
                325                 330                 335

Phe Cys Asp Phe Arg Ser Arg Asp Asp Tyr Glu Thr Ile Ala Met
            340                 345                 350

Ser Thr Met His Thr Asp Val Ser Lys Thr Ser Leu Lys Gln Ala Ser
        355                 360                 365

Pro Val Ala Phe Lys Lys Ile Asn Asn Asn Asp Asn Glu Lys Ile
370                 375                 380

<210> SEQ ID NO 32
<211> LENGTH: 413
<212> TYPE: PRT
<213> ORGANISM: Homo sapiens

<400> SEQUENCE: 32

Met Gly Gln Pro Gly Asn Gly Ser Ala Phe Leu Leu Ala Pro Asn Arg
 1               5                  10                  15

Ser His Ala Pro Asp His Asp Val Thr Gln Gln Arg Asp Glu Val Trp
                20                  25                  30

Val Val Gly Met Gly Ile Val Met Ser Leu Ile Val Leu Ala Ile Val
            35                  40                  45

Phe Gly Asn Val Leu Val Ile Thr Ala Ile Ala Lys Phe Glu Arg Leu
        50                  55                  60
```

```
Gln Thr Val Thr Asn Tyr Phe Ile Thr Ser Leu Ala Cys Ala Asp Leu
 65                  70                  75                  80

Val Met Gly Leu Ala Val Val Pro Phe Gly Ala Ala His Ile Leu Met
                 85                  90                  95

Lys Met Trp Thr Phe Gly Asn Phe Trp Cys Glu Phe Trp Thr Ser Ile
            100                 105                 110

Asp Val Leu Cys Val Thr Ala Ser Ile Glu Thr Leu Cys Val Ile Ala
        115                 120                 125

Val Asp Arg Tyr Phe Ala Ile Thr Ser Pro Phe Lys Tyr Gln Ser Leu
    130                 135                 140

Leu Thr Lys Asn Lys Ala Arg Val Ile Ile Leu Met Val Trp Ile Val
145                 150                 155                 160

Ser Gly Leu Thr Ser Phe Leu Pro Ile Gln Met His Trp Tyr Arg Ala
                165                 170                 175

Thr His Gln Glu Ala Ile Asn Cys Tyr Ala Asn Glu Thr Cys Cys Asp
            180                 185                 190

Phe Phe Thr Asn Gln Ala Tyr Ala Ile Ala Ser Ser Ile Val Ser Phe
        195                 200                 205

Tyr Val Pro Leu Val Ile Met Val Phe Val Tyr Ser Arg Val Phe Gln
    210                 215                 220

Glu Ala Lys Arg Gln Leu Gln Lys Ile Asp Lys Ser Glu Gly Arg Phe
225                 230                 235                 240

His Val Gln Asn Leu Ser Gln Val Glu Gln Asp Gly Arg Thr Gly His
                245                 250                 255

Gly Leu Arg Arg Ser Ser Lys Phe Cys Leu Lys Glu His Lys Ala Leu
            260                 265                 270

Lys Thr Leu Gly Ile Ile Met Gly Thr Phe Thr Leu Cys Trp Leu Pro
        275                 280                 285

Phe Phe Ile Val Asn Ile Val His Val Ile Gln Asp Asn Leu Ile Arg
    290                 295                 300

Lys Glu Val Tyr Ile Leu Leu Asn Trp Ile Gly Tyr Val Asn Ser Gly
305                 310                 315                 320

Phe Asn Pro Leu Ile Tyr Cys Arg Ser Pro Asp Phe Arg Ile Ala Phe
                325                 330                 335

Gln Glu Leu Leu Cys Leu Arg Arg Ser Ser Leu Lys Ala Tyr Gly Asn
            340                 345                 350

Gly Tyr Ser Ser Asn Gly Asn Thr Gly Glu Gln Ser Gly Tyr His Val
        355                 360                 365

Glu Gln Glu Lys Glu Asn Lys Leu Leu Cys Glu Asp Leu Pro Gly Thr
    370                 375                 380

Glu Asp Phe Val Gly His Gln Gly Thr Val Pro Ser Asp Asn Ile Asp
385                 390                 395                 400

Ser Gln Gly Arg Asn Cys Ser Thr Asn Asp Ser Leu Leu
                405                 410

<210> SEQ ID NO 33
<211> LENGTH: 346
<212> TYPE: PRT
<213> ORGANISM: artificial sequence
<220> FEATURE:
<223> OTHER INFORMATION: macaque MCH2R/MCH1R N-terminal chimera -
      alternate sequence

<400> SEQUENCE: 33

Met Asp Leu Glu Ala Ser Leu Leu Pro Thr Gly Pro Asn Thr Ser Asn
```

```
              1               5                  10                 15
        Thr Ser Asp Gly Pro Asp Asn Leu Thr Ser Ala Gly Ser Pro Pro Arg
                    20                  25                  30

Ser Gly Ser Val Ser Tyr Ile Asn Val Ile Leu Pro Ser Met Ile Gly
                    35                  40                  45

Ile Ile Cys Ser Thr Gly Leu Val Gly Asn Ile Leu Ile Val Phe Thr
        50                  55                  60

Ile Ile Arg Ser Arg Lys Lys Thr Val Pro Asp Ile Tyr Ile Cys Asn
        65                  70                  75                  80

Leu Ala Val Ala Asp Leu Val His Ile Val Gly Met Pro Phe Leu Ile
                        85                  90                  95

His Gln Trp Ala Arg Gly Gly Glu Trp Val Phe Gly Gly Pro Leu Cys
                        100                 105                 110

Thr Ile Ile Thr Ser Leu Asp Thr Cys Asn Gln Phe Ala Cys Ser Ala
                        115                 120                 125

Ile Met Thr Val Met Ser Val Asp Arg Tyr Phe Ala Leu Val Gln Pro
                        130                 135                 140

Phe Arg Leu Thr Ser Trp Arg Thr Arg Tyr Lys Thr Ile Arg Ile Asn
        145                 150                 155                 160

Leu Gly Leu Trp Ala Ala Ser Phe Ile Leu Ala Leu Pro Val Trp Ile
                        165                 170                 175

Tyr Ser Lys Val Ile Lys Phe Lys Asp Gly Val Glu Ser Cys Ala Phe
                        180                 185                 190

Asp Leu Thr Ser Pro Asp Asp Val Leu Trp Tyr Thr Leu Tyr Leu Thr
                        195                 200                 205

Ile Thr Thr Phe Phe Pro Leu Pro Leu Ile Leu Val Cys Tyr Ile
        210                 215                 220

Leu Ile Leu Cys Tyr Thr Trp Glu Met Tyr Gln Gln Asn Lys Asp Ala
        225                 230                 235                 240

Arg Cys Cys Asn Pro Ser Val Pro Lys Gln Arg Val Met Lys Leu Thr
                        245                 250                 255

Lys Met Val Leu Val Leu Val Ala Val Phe Ile Leu Ser Ala Ala Pro
                    260                 265                 270

Tyr His Val Ile Gln Leu Val Asn Leu Gln Met Glu Gln Pro Thr Leu
                    275                 280                 285

Ala Phe Tyr Val Gly Tyr Tyr Leu Ser Ile Cys Leu Ser Tyr Ala Ser
                    290                 295                 300

Ser Ser Ile Asn Pro Phe Leu Tyr Ile Leu Leu Ser Gly Asn Phe Gln
        305                 310                 315                 320

Lys Arg Leu Pro Gln Ile Gln Arg Arg Val Thr Asp Lys Glu Ile Lys
                    325                 330                 335

Asn Met Gly Asn Thr Leu Lys Ser His Phe
                    340                 345

<210> SEQ ID NO 34
<211> LENGTH: 334
<212> TYPE: PRT
<213> ORGANISM: artificial sequence
<220> FEATURE:
<223> OTHER INFORMATION: Macaque MCH2/MCH1 IC3 loop chimera -
      alternate sequence

<400> SEQUENCE: 34

Met Asn Pro Phe His Ser Ser Cys Trp Asn Thr Ser Ala Glu Leu Ser
1               5                   10                  15
```

-continued

```
Asn Lys Ser Trp Asn Lys Glu Phe Ala Tyr Gln Thr Ala Ser Val Val
         20              25              30

Asp Thr Val Ile Leu Pro Ser Met Ile Gly Ile Ile Cys Ser Thr Gly
         35              40              45

Leu Val Gly Asn Ile Leu Ile Val Phe Thr Ile Ile Arg Ser Arg Lys
         50              55              60

Lys Thr Val Pro Asp Ile Tyr Ile Cys Asn Leu Ala Val Ala Asp Leu
65                   70              75              80

Val His Ile Val Gly Met Pro Phe Leu Ile His Gln Trp Ala Arg Gly
             85              90              95

Gly Glu Trp Val Phe Gly Gly Pro Leu Cys Thr Ile Ile Thr Ser Leu
             100             105             110

Asp Thr Cys Asn Gln Phe Ala Cys Ser Ala Ile Met Thr Val Met Ser
         115             120             125

Val Asp Arg Tyr Phe Ala Leu Val Gln Pro Phe Arg Leu Thr Ser Trp
130              135             140

Arg Thr Arg Tyr Lys Thr Ile Arg Ile Asn Leu Gly Leu Trp Ala Ala
145                  150             155             160

Ser Phe Ile Leu Ala Leu Pro Val Trp Ile Tyr Ser Lys Val Ile Lys
             165             170             175

Phe Lys Asp Gly Val Glu Ser Cys Ala Phe Asp Leu Thr Ser Pro Asp
             180             185             190

Asp Val Leu Trp Tyr Thr Leu Tyr Leu Thr Ile Thr Thr Phe Phe Phe
         195             200             205

Pro Leu Pro Leu Ile Leu Val Cys Tyr Ile Leu Ile Leu Gln Arg Met
         210             215             220

Thr Ser Ser Val Ala Pro Ala Ser Gln Arg Ser Ile Arg Leu Arg Thr
225              230             235             240

Lys Arg Leu Thr Lys Met Val Leu Val Leu Val Ala Val Phe Ile Leu
             245             250             255

Ser Ala Ala Pro Tyr His Val Ile Gln Leu Val Asn Leu Gln Met Glu
             260             265             270

Gln Pro Thr Leu Ala Phe Tyr Val Gly Tyr Tyr Leu Ser Ile Cys Leu
         275             280             285

Ser Tyr Ala Ser Ser Ser Ile Asn Pro Phe Leu Tyr Ile Leu Leu Ser
         290             295             300

Gly Asn Phe Gln Lys Arg Leu Pro Gln Ile Gln Arg Arg Val Thr Asp
305              310             315             320

Lys Glu Ile Lys Asn Met Gly Asn Thr Leu Lys Ser His Phe
             325             330
```

MONKEY AND CANINE MELANIN CONCENTRATING HORMONE RECEPTORS

CROSS-REFERENCE TO RELATED APPLICATIONS

This application claims priority to U.S. Provisional Application No. 60/350,493, filed Nov. 13, 2001.

FIELD OF THE INVENTION

The present invention relates generally to the treatment of conditions associated with melanin concentrating hormone receptor activation in humans and other animals. The invention is more specifically related to polypeptides comprising MCH receptor sequences and to polynucleotides encoding such polypeptides. Such polypeptides and polynucleotides may be used in the identification of agents that modulate MCH receptor activity.

DESCRIPTION OF THE SEQUENCE LISTING

SEQ ID NO:1 Cynomolgus macaque MCH2R clone A—DNA sequence
SEQ ID NO:2 Cynomolgus macaque MCH2R clone A—amino acid sequence
SEQ ID NO:3 Cynomolgus macaque MCH2R clone B—DNA sequence
SEQ ID NO:4 Cynomolgus macaque MCH2R clone B—amino acid sequence
SEQ ID NO:5 Cynomolgus macaque MCH2R sequence (with Pro at residue 38)
SEQ ID NO:6 Canine MCH2R DNA sequence
SEQ ID NO:7 Canine MCH2R amino acid sequence
SEQ ID NO:8 5' Forward Outer Primer
SEQ ID NO:9 879R Reverse Primer
SEQ ID NO:10 509 Forward Primer
SEQ ID NO:11 3' Reverse Outer Primer
SEQ ID NO:12 5' Kozak cloning primer
SEQ ID NO:13 His-6×(hexa-histidine) epitope
SEQ ID NO:14 FLAG epitope
SEQ ID NO:15 Amino acid sequence of macaque MCH2R/MCH1R C-terminal chimera A
SEQ ID NO:16 Amino acid sequence of macaque MCH2R/MCH1R C-terminal chimera B
SEQ ID NO:17 Amino acid seq. of macaque MCH2R/canine MCH2R C-term chimera A
SEQ ID NO:18 Amino acid seq. of macaque MCH2R/canine MCH2R C-term chimera B
SEQ ID NO:19 Amino acid seq. of macaque MCH2R/human $NPY_1$ C-term chimera
SEQ ID NO:20 Amino acid seq. of macaque MCH2R/human beta-2 adrenergic C-term chimera
SEQ ID NO:21 Amino acid sequence of macaque MCH2R/MCH1R N-terminal chimera A
SEQ ID NO:22 Amino acid seq. of macaque MCH2R/canine MCH2R N-term chimera A
SEQ ID NO:23 Amino acid sequence of macaque MCH2R/MCH1R N-terminal chimera B
SEQ ID NO:24 Amino acid seq. of macaque MCH2R/canine MCH2R N-term chimera B
SEQ ID NO:25 Amino acid sequence of macaque MCH2R/MCH1R IC3 loop chimera
SEQ ID NO:26 Amino acid seq. of macaque MCH2R/canine MCH2R IC3 loop chimera
SEQ ID NO:27 Amino acid seq. of macaque MCH2R/human $NPY_1$ IC3 loop chimera
SEQ ID NO:28 Amino acid seq. of macaque MCH2R/human beta-2 adrenergic IC3 chimera
SEQ ID NO:29 Amino acid sequence of human MCH2R
SEQ ID NO:30 Amino acid sequence of cynomolgus macaque MCH1R
SEQ ID NO:31 Amino acid sequence of human neuropeptide $Y_1$ ($NPY_1$) receptor
SEQ ID NO:32 Amino acid sequence of human beta-2 adrenergic receptor
SEQ ID NO:33 Amino acid sequence of alternate macaque MCH2R/MCH1R N-terminal chimera
SEQ ID NO:34 Amino acid sequence of alternate macaque MCH2R/MCH1R IC3 loop chimera

BACKGROUND OF THE INVENTION

Melanin concentrating hormone, or MCH, is a cyclic 19 amino acid neuropeptide that functions as a regulator of food intake and energy balance. In many vertebrate species, including humans, MCH is produced in the hypothalamus, which is associated with behaviors such as eating, drinking, aggression and sexual behavior. MCH is also produced at various peripheral sites, including the gastrointestinal tract and testis.

The postulated role of MCH in feeding behavior and body weight is confirmed by the finding that i.c.v. injection of MCH into the lateral ventrical of the hypothalamus increases caloric consumption in rats over similarly treated control animals. Furthermore, rats having the ob/ob genotype exhibit a 50–80% increase in MCH mRNA expression as compared to leaner ob/+ genotype mice. MCH knockout mice are leaner than mice that produce MCH, but are otherwise genetically identical, due to hypophagia and an increased metabolic rate.

MCH activity is mediated via binding to specific receptors. Like other G protein-coupled receptors (e.g., neuropeptide Y (NPY) and beta-adrenergic receptors), MCH receptors are membrane-spanning proteins that consist of a single contiguous amino acid chain comprising an extracellular N-terminal domain, seven membrane-spanning alpha helical domains (connected by three intracellular loop domains alternating with three extracellular loop domains), and an intracellular C-terminal domain. Signal transduction is initiated by the binding of MCH to the receptor. This elicits conformational changes in the extracellular domains. When the receptor is functioning properly, these conformational changes propagate through the transmembrane domains and result in a coordinated change in the intracellular portions of the receptor. This precise alteration in the intracellular domains acts to trigger the associated G-protein complex to modulate intracellular signaling.

MCH1R is a 353 amino acid, 7-transmembrane, alpha-helical, G protein-coupled receptor, initially reported as orphan receptor SCL-1 by Kolakowski et al. (1996) *FEBS Lett.* 398:253–58 and Lakaye et al. (1998) *Biochim. Biophys. Acta* 1401:216–220. Chambers et al. (1999) *Nature* 400:261–65 and Saito et al. (1999) *Nature* 400:265–69 subsequently showed that SLC-1 was an MCH receptor. Immunohistochemistry studies of rat brain sections indicate that the MCH1R is widely expressed in brain. MCH1R expression is found in olfactory tubercle, cerebral cortex, substantia nigra, basal forebrain CA1, CA2, and CA3 field of the hippocampus, amygdala, and in nuclei of the hypothalamus, thalamus, midbrain and hindbrain. Strong signals are observed in the ventromedial and dorsomedial nuclei of the hypothalamus, two areas of the brain involved in feeding behavior. Upon binding MCH, MCH1R expressed in HEK 293 cells mediate a dose dependent release of intracellular calcium. Cells expressing MCH1R also exhibit a pertussis toxin sensitive dose-dependent inhibition of forskolin-elevated cyclic AMP, indicating that the receptor couples to a $G_{I/O}$ G-protein alpha subunit.

Recently, a second MCH receptor (designated MCH2R) was identified (WO 01/70975; WO 01/07606; WO 00/49046; An et al., Proc. Natl. Acad. Sci. USA (2001) 98:7576–7581; Sailer et al., Proc. Natl. Acad. Sci. USA (2001) 98:7564–7569; Hill et al., J. Biol. Chem. (2001) 276:20125–20129; Mori et al., Biochem. Biophys. Res. Commun. (2001) 283:1013–1018). The human sequence (Hill et al.) has GenBank Accession Number AF347063. MCH2R has an overall amino acid identity of more than 30% with MCH1R, and is detected specifically in the same regions of the brain as MCH1R.

Agents capable of modulating MCH receptor activity are highly desirable for the treatment of obesity, eating disorders (e.g., bulimia and anorexia), sexual disorders (e.g., anorgasmic or psychogenic impotence) and metabolic disorders, such as diabetes. Isolated MCH receptors (e.g., as components of membrane preparations), cells expressing such receptors and cloned MCH receptor genes are needed to facilitate the discovery of such agents.

Accordingly, there is a need in the art for additional MCH receptor sequences. The present invention fulfills this need, and provides further related advantages.

SUMMARY OF THE INVENTION

Briefly stated, the present invention provides compositions and methods for the identification of therapeutic agents useful for treating conditions associated with MCH receptor activation. In one aspect, the present invention provides isolated MCH2R polypeptides, comprising a monkey or canine MCH2R sequence. Within certain embodiments, the polypeptide comprises at least 310, at least 325 or 340 consecutive amino acids of the cynomolgus macaque (*Macaca jascicularis*) sequence provided in SEQ ID NO:2 or 4. Within other embodiments, the polypeptide comprises at least 70, at least 100, at least 300, at least 315 or 330 consecutive amino acids of a canine MCH2R sequence recited in SEQ ID NO:7.

Within related aspects, the present invention provides MCH2R chimeric polypeptides that comprise a monkey or canine MCH2R sequence as described above, wherein one or more domains are replaced with a corresponding domain of a different C protein-coupled receptor. Preferably, from 1 to 3 domains are replaced; more preferably 1 domain is replaced. For example, the intracellular loop 3, N-terminal domain or C-terminal domain of monkey or canine MCH2R may be replaced with a corresponding domain of MCH1R, $NPY_1$ receptor, beta-2-adrenergic receptor or MCH2R from a different species. Representative chimeric polypeptides include those provided in SEQ ID NOs:15–28, 33 and 34. Chimeric monkey or canine MCH1R polypeptides in which the third intracellular loop, N-terminal region and/or C-terminal region of MCH1R are replaced by the corresponding region of monkey or canine MCH2R are also provided.

Within further aspects, the present invention provides isolated polynucleotides (which may be DNA or RNA) that encode an MCH2R polypeptide or chimeric polypeptide as described above. Such polynucleotides may comprise a native sequence (e.g., SEQ ID NO:1, 3, 5 or 6) or may contain one or more changes relative to the native sequence that do not affect the sequence of the encoded polypeptide. Certain such polynucleotides comprise (i) at least 930 consecutive nucleotides of SEQ ID NO:1, 3 or 5; or (ii) at least 210, at least 300 or at least 900 consecutive nucleotides of SEQ ID NO:6.

The present invention further provides expression vectors (e.g., plasmids and viral vectors) that comprise a polynucleotide as described above, as well as transgenic host cells that express a polypeptide as described above (e.g., transformed or transfected with at least one such expression vector) and cell membrane preparations isolated from such transgenic cells.

Methods are also provided herein for determining MCH receptor binding activity of a compound, comprising the steps of: (a) contacting a compound with a cell membrane preparation as described above; and (b) detecting binding of the compound to the cell membrane preparation. Binding may be detected, for example, by measuring competition for binding with detectably labeled MCH.

Within further aspects, the present invention provides methods for detecting MCH receptor modulating activity of a compound, comprising the steps of: (a) contacting a compound with transgenic cells as described above; (b) detecting a level of $Ca^{2+}$ in the contacted cells; and (c) comparing the detected level of $Ca^{2+}$ with a level of $Ca^{2+}$ detected in control transgenic cells in the absence of compound. Within certain embodiments, before step (a), the transgenic cells are: (i) contacted with an indicator of intracellular $Ca^{2+}$ concentration to yield indicator-loaded cells; and (ii) washed. The level of $Ca^{2+}$ may be detected, for example, by quantifying $Ca^{2+}$ concentration-dependent changes in the properties of the indicator of intracellular $Ca^{2+}$.

Also provided herein are methods for detecting MCH receptor agonist activity of a compound, comprising the steps of: (a) contacting transgenic cells as described above with an indicator of intracellular $Ca^{2+}$ concentration, to yield indicator-loaded cells; (b) washing the indicator-loaded cells; (c) contacting a portion of the washed, indicator-loaded cells with a compound to yield test cells; (d) separately detecting a property of the indicator of intracellular $Ca^{2+}$ concentration in the test cells and in a second portion of the washed and indicator-loaded cells; and (e) comparing the detected property of the test cells with the detected property of the washed indicator-loaded cells.

The present invention further provides methods for detecting MCH receptor antagonist activity of a compound, comprising the steps of: (a) contacting a compound and an MCH receptor agonist with transgenic cells as described above; (b) detecting a level of $Ca^{2+}$ in the contacted cells; and (c) comparing the detected level of $Ca^{2+}$ with a level of $Ca^{2+}$ detected in control cells in the presence of agonist and in the absence of compound.

Within related aspects, methods are provided for detecting MCH receptor antagonist activity of a compound, comprising the steps of: (a) contacting transgenic cells as described above with an indicator of intracellular $Ca^{2+}$ concentration, to yield indicator-loaded cells; (b) washing the indicator-loaded cells; (c) contacting a first portion of the washed, indicator-loaded cells with a compound and an MCH receptor agonist to yield test cells; (d) contacting a second portion of the washed, indicator-loaded cells with an MCH receptor agonist to yield control cells; (e) separately detecting a property of the indicator of intracellular $Ca^{2+}$ in the test cells and in the control cells; and (f) comparing the detected property of the test cells with the detected property of the control cells.

These and other aspects of the present invention will become apparent upon reference to the following detailed description and attached drawings.

BRIEF DESCRIPTION OF THE DRAWINGS

FIGS. 1A to 1C depict an alignment of the amino acid sequences of (a) human MCH2R (SEQ ID NO:29), (b) cynomolgus macaque MCH2R clone A (SEQ ID NO:2), (c) cynomolgus macaque MCH2R clone B (SEQ ID NO:4) and (d) canine MCH2R (SEQ ID NO:7).

DETAILED DESCRIPTION OF THE INVENTION

Figure 2:
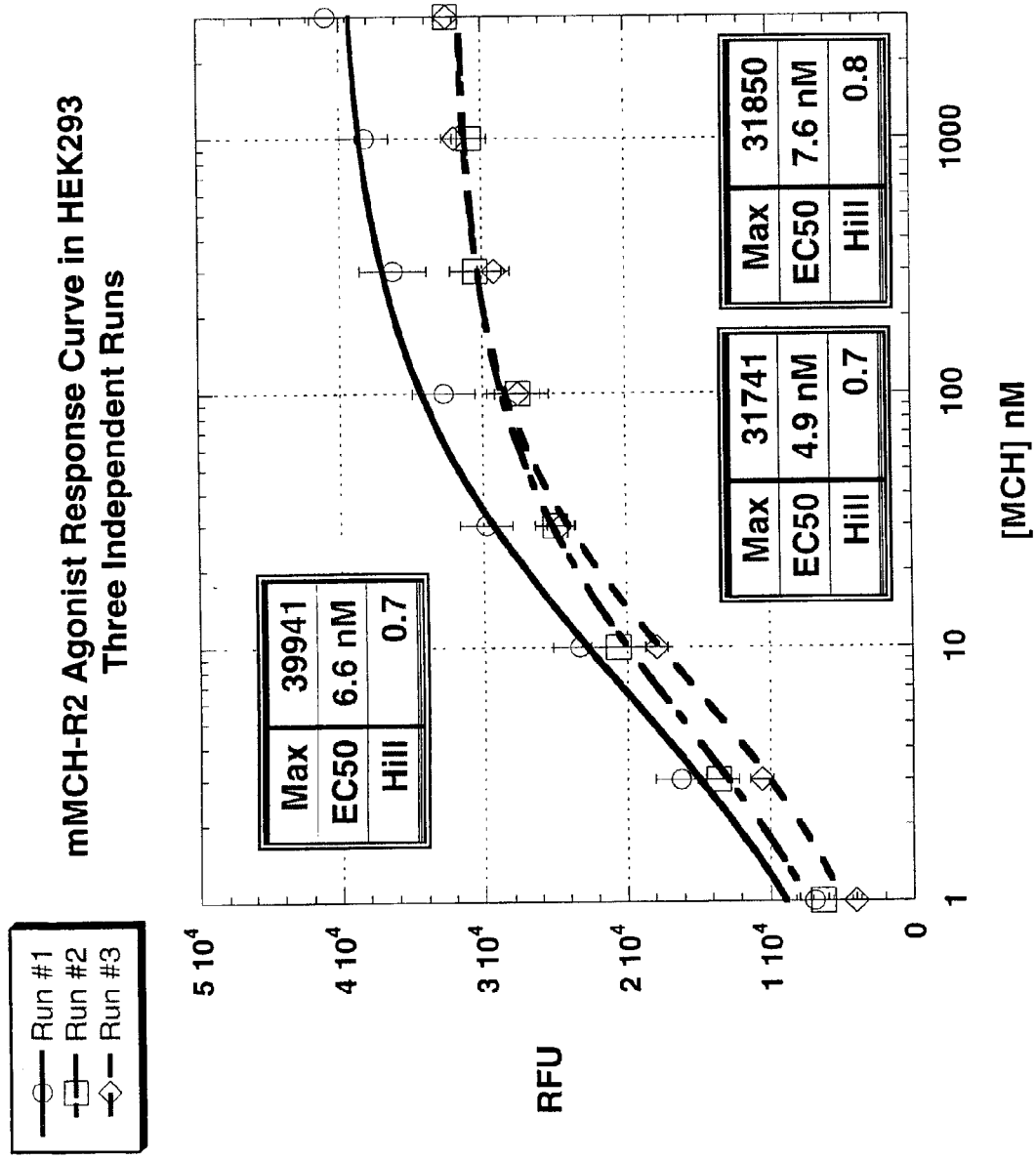
FIG. 2 is a graph depicting the results of three independent functional assays performed using HEK 293 cells expressing cynomolgus macaque MCH2R to determine the $EC_{50}$ of MCH. Fluorescence response (excitation at 480 nM and emission at 530 nM) is presented as relative fluorescence units (RFU) as a function of MCH concentration (in nM).

As noted above, the present invention is generally directed to compounds and methods for identifying therapeutic agents useful for treating conditions associated with MCH receptor activation. Compounds provided herein include MCH receptor polynucleotides, which comprise a monkey or canine MCH2R sequence, and MCH receptor polypeptides (including chimeric polypeptides) encoded by such polynucleotides. MCH receptor polypeptides and polynucleotides may be used to identify therapeutic agents, as discussed in further detail below.

MCH Receptor Polypeptides

In certain aspects, the present invention provides isolated monkey and canine MCH2R polypeptides, as well as chimeric polypeptides. Cynomolgus macaque MCH2R polypeptides generally comprise at least 310, preferably at least 325 and more preferably 340, consecutive amino acids of a cynomolgus macaque MCH2R sequence provided in SEQ ID NO:2 (version A) or SEQ ID NO:4 (version B). MCH2R versions A and B are identical except for position 38, which is Pro in version A and Leu in version B. Canine MCH2R polypeptides generally comprise at least at least 70, at least 100, at least 300, at least 315 or 330 consecutive amino acids of a canine MCH2R sequence, such as that provided in SEQ ID NO:7. Amino acid deletions, additions and/or substitutions may occur at any point in the naturally-occurring sequence (e.g., polypeptides with deletions at the C-terminus and polypeptides that comprise an antibody recognition sequence) provided that such modifications do not substantially diminish receptor function, as determined using an assay in Example 5. A substitution does not "substantially diminish" receptor function if the activity within a calcium mobilization assay as provided herein is enhanced, unchanged or diminished by no more than 10%. Amino acid substitutions may be made within cynomolgus macaque and canine MCH2R sequences provided herein at up to 15 amino acid residues, preferably at no more than 10 residues and more preferably at no more than 5 residues. Any substitutions preferably do not result in a human MCH2R sequence (FIG. 1; SEQ ID NO:29). For cynomolgus macaque MCH2R, the valine residues at positions 31 and 84 and the proline or leucine at position 38 should not be substituted.

Substitutions may, but need not, be conservative. A "conservative substitution" is one in which an amino acid is substituted for another amino acid that has similar properties, such that one skilled in the art of peptide chemistry would expect the secondary structure and hydropathic nature of the polypeptide to be substantially unchanged. Such substitutions may generally be made on the basis of similarity in polarity, charge, solubility, hydrophobicity, hydrophilicity and/or the amphipathic nature of the residues. For example, negatively charged amino acids include asp and glu; positively charged amino acids include lys and arg; and amino acids with uncharged polar head groups having similar hydrophilicity values include leu, ile and val; gly and ala; asn and gln; and ser, thr, phe and tyr. Other groups of amino acids that may represent conservative changes include: (1) Ala, Pro, Gly, Glu, Asp, Gln, Asn, Ser, Thr; (2) Cys, Ser, Tyr, Thr; (3) Val, Ile, Leu, Met, Ala, Phe; (4) Lys, Arg, His; and (5) Phe, Tyr, Trp, His.

Chimeric MCH2R polypeptides are those in which at least one domain is derived from a macaque or canine MCH2R sequence, with one or more domains replaced with corresponding domain(s) from a different G protein-coupled receptor. Chimeric polypeptides include, for example, macaque and canine MCH2R/MCH1R intracellular loop 3 chimeras (i.e., MCH2R receptors in which the amino acid sequence of the third intracellular loop has been replaced by the amino acid sequence of the third intracellular loop of macaque or canine MCH1R), macaque and canine MCH2R/MCH1R C-terminal chimeras, and macaque and canine MCH2R/MCH1R N-terminal chimeras. Alternatively, the intracellular loop 3, N-terminal or C-terminal region of MCHR2 may be replaced with a corresponding region of $NPY_1$, beta-2 adrenergic receptor or MCH2R from a different species. Chimeric macaque and canine MCH1R polypeptides in which the third intracellular loop, N-terminal region and/or C-terminal region of MCH1R are replaced by the corresponding region of MCH2R are also contemplated.

As noted above, MCH receptors contain an N terminal domain, seven transmembrane domains interspersed with three intracellular loop domains alternating with three extracellular loop domains, and an intracellular C-terminal domain. The precise locations of domains may be conveniently calculated by computer analysis of hydrophobicity or hydrophilicity using hydropathy profiles, such as standard Kyte-Doolittle analysis (Kyte and Doolittle, *J. Mol. Biol.* 157:105–32, 1982). The transition boundaries between the hydrophobic and hydrophilic domains are typically marked by the presence of charged or polar (hydrophilic) amino acid residues at the beginning or end of a stretch of nonpolar (hydrophobic) residues. The N-terminus extends into the extracellular space and the C-terminus into the cell cytoplasm. Each of the seven hydrophobic domains is about 20–25 amino acids long, assumes a largely alpha helical conformation, and crosses once through the plasma membrane, its entire extent generally embedded in the membrane. The hydrophobic domains are thus also referred to as transmembrane domains or membrane-spanning alpha helical domains, while the hydrophilic domains are referred to as either extracellular or intracellular domains, depending upon their predicted locations in a functional, membrane-bound receptor. The hydrophilic domains interconnecting transmembrane domains form loops within the cytoplasm or extracellular space, and are consequently referred to as cytoplasmic or extracellular loop domains.

G protein-coupled receptors, including MCH receptors, have been structurally modeled as to secondary and tertiary structural conformation, and the precise locations of the extracellular, transmembrane and intracellular domains within their primary structures (i.e., their amino acid sequences) are well known and generally agreed to in the art. The location of G protein-coupled receptor domains may be determined using the model of Baldwin (*EMBO J.* 12:1693–703, 1993), in which certain conserved residues are initially located and aligned. For constructing chimeric polypeptides provided herein, locations of domains within MCH2R polypeptides are generally as follows: extracellular N-terminal (residues 1 to 34), seven transmembrane domains (approximately residues 35–60; 66–91; 107–132; 148–173; 196–221; 249–274 and 286–311, respectively) interspersed with three intracellular loop domains alternating with three extracellular loop domains, and intracellular C-terminal domain (residues 312 to end). Intracellular loop 3 consists of residues 222 to 248. Any of these domains may be replaced with a corresponding domain from MCH1R of the same species, MCH1R or MCH2R of a different species, or a non-MCH receptor such as $NPY_1$ or beta-2 adrenergic receptor. It will be apparent that, when replacing one domain with another, the residue numbers provided above may be altered slightly in either direction in order to facilitate cloning. In general, residue numbers may be altered by up to 6, preferably up to 4, amino acid residues. For example, if intracellular loop 3 (IC3) is to be replaced, the replaced portion may begin at any residue between 216 and 228, and may end at any residue between 242 and 254. Preferred macaque or canine MCH2R IC3 chimeras contain residues 1–221 or 1–223 and 247-end or 249-end of MCH2R, with residues corresponding to MCH2R 222 or 224 through 246 or 248 derived from a different G protein-coupled receptor. Similarly, the C-terminal domain may be replaced beginning at any residue between 306 and 318, preferably beginning at residue 314 or 317. When replacing the N-terminal domain, the portion replaced may end at any residue between 28 and 44, preferably at 28, 31 or 36. Corresponding domains of other G protein-coupled receptors may be readily identified by performing an alignment of the receptor sequence with an MCH2R sequence provided herein.

Chimeric polypeptides include those in which one or more of the intracellular loop 3, the N-terminal domain or the C-terminal domain is replaced. The sequences of certain representative chimeras are summarized in Table I and recited in SEQ ID NOs:15–28, 33 and 34. More specifically, representative chimeras in which a single domain within MCH2R is replaced with a corresponding MCH1R domain are provided in SEQ ID NOs:15, 16, 21, 23, 25, 33 and 34. Similar chimeras may be prepared by substituting a single domain within MCH1R with the corresponding MCHR2 domain. Representative chimeras in which a single MCH2R domain is replaced with an MCH2R domain from another species include SEQ ID NOs:17, 18, 22, 24 and 26. Representative chimeras in which a single MCH2R domain is replaced with the corresponding domain from a G protein-coupled receptor other than an MCH receptor include SEQ ID NOs:19, 20, 27 and 28. It will be apparent that similar chimeras may be prepared using canine sequences instead of macaque sequences.

TABLE I

Representative Cynomolgus Macaque MCH2R Chimeras

| SEQ ID NO. | MCH2R Residues (SEQ ID NO:2) | Inserted Domain |
|---|---|---|
| 15 | 1–316 | Macaque MCH1R (SEQ ID NO:30) 322–353 (C-terminal) |
| 16 | 1–313 | Macaque MCH1R (SEQ ID NO:30) 319–353 (C-terminal) |
| 17 | 1–316 | Canine MCH2R (SEQ ID NO:7) 317–330 (C-terminal) |
| 18 | 1–313 | Canine MCH2R (SEQ ID NO:7) 314–330 (C-terminal) |
| 19 | 1–316 | Human NPY1 (SEQ ID NO:31) 331–384 (C-terminal) |
| 20 | 1–316 | Human beta-2 adrenergic receptor (SEQ ID NO:32) 345–413 (C-terminal) |
| 21 | 29–340 | Macaque MCH1R (SEQ ID NO:30) 1–34 (N-terminal) |
| 22 | 29–340 | Canine MCH2R (SEQ ID NO:7) 1–28 (N-terminal) |
| 23 | 32–340 | Macaque MCH1R (SEQ ID NO:30) 1–37 (N-terminal) |
| 24 | 32–340 | Canine MCH2R (SEQ ID NO:7) 1–31 (N-terminal) |
| 25 | 1–223; 247–340 | Macaque MCH1R (SEQ ID NO:30) 235–251 (IC3) |
| 26 | 1–223; 247–340 | Canine MCH2R (SEQ ID NO:7) 224–246 (IC3) |
| 27 | 1–223; 247–340 | Human NPY1 (SEQ ID NO:31) 238–258 (IC3) |
| 28 | 1–223; 247–340 | Human beta-2 adrenergic receptor (SEQ ID NO:32) 226–268 (IC3) |
| 33 | 35–340 | Macaque MCH1R (SEQ ID NO:30) 1–40 (N-terminal) |
| 34 | 1–221; 248–340 | Macaque MCH1R (SEQ ID NO:30) 234–253 (IC3) |

MCH receptor polypeptides may be prepared using any of a variety of well known techniques from transgenic cells (i.e., cells that have been genetically altered to express an MCH receptor polypeptide). Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with at least one expression vector containing a DNA molecule that encodes a recombinant polypeptide. Suitable host cells include prokaryotes, yeast and higher eukaryotic cells, such as mammalian or plant cells. For example, *E. coli*, yeast, amphibian oocytes and mammalian cell lines such as COS, CHO, BHK, HEK 293, VERO, HeLa, MDCK, WI38 or NIH 3T3 cells may be used. Insect cell systems infected with recombinant virus expression vectors (for example, baculovirus) comprising a MCH1R polynucleotide provided herein may also be employed. Alternatively, a transgenic cell may be isolated from a transgenic animal.

MCH receptor polypeptides are preferably isolated. A polypeptide is said to be "isolated" if it represents at least 1% of total polypeptide molecules, preferably at least 10% and more preferably at least 20% of total polypeptide molecules, within a sample or preparation).

Within certain embodiments, MCH receptor polypeptides are isolated as membrane preparations. Such preparations are generated from transgenic cells that express an MCH receptor polypeptide, using any standard procedure. For example, transfected host cell pellets may be homogenized and centrifuged (e.g., 10 minutes at 48,000×g). The supernatant is discarded and the pellet is resuspended and homogenized again to generate an isolated membrane preparation. A more detailed protocol is provided in Example 3 herein. Preferably, isolated membranes have an MCH binding activity that is at least 2-fold greater, preferably 10-fold greater and more preferably at least 20-fold greater than that exhibited by control membranes isolated from a control cell (e.g., an untransfected cell of the same cell line used to prepare the recombinant cell or a cell transfected with a control vector that does not encode an MCH receptor polypeptide). Preferred membranes contain at least 0.1 pmol, 1 pmol or 5 pmol of MCH receptor polypeptide per mg of total membrane protein.

A tagged fusion protein may be purified using an antibody specific for the tag (e.g., by affinity chromatography). Such purification procedures may require detergent extraction, which may result in a decrease in signal transduction activity. The resulting purified proteins are useful as antigens for the preparation of receptor-specific antibodies.

Chimeric proteins may be prepared using standard recombinant methods. For example, convenient restriction sites may be incorporated into an MCH2R polynucleotide using site-directed mutagenesis. This allows the removal of polynucleotide encoding a particular domain. The domain to be inserted may be synthesized, and ligated to the digested MCH2R polynucleotide. The resulting polynucleotide encodes the chimeric polypeptide, and may be expressed as described herein. A similar process may be used to generate polypeptides that comprise a single MCH2R domain, inserted into a different G protein-coupled receptor.

MCH Receptor Polynucleotides

Any polynucleotide that encodes an MCH2R polypeptide (e.g., naturally occurring or chimeric) as described herein is encompassed by the present invention. Polynucleotides may be single-stranded (coding or antisense) or double-stranded, and may be DNA (genomic, cDNA or synthetic) or RNA, such as mRNA molecules. Additional coding or non-coding sequences may, but need not, be present within a polynucleotide of the present invention, and a polynucleotide may, but need not, be linked to other molecules and/or support materials.

Certain polynucleotides encode a cynomolgus macaque MCH2R polypeptide. Such polynucleotides encode at least a portion of a native cynomolgus macaque MCH2R sequence, such as the MCH2R sequence provided in SEQ ID NO:2 (version A) or SEQ ID NO:4 (version B). In certain embodiments, such a polynucleotide encodes at least 310, at least 325 or 340 consecutive amino acids of a cynomolgus macaque MCH2R protein sequence provided in SEQ ID NO:2 or SEQ ID NO:4. For less than full length MCH2R sequences, deletions may be made at any point in the naturally-occurring sequence, such as at the 3' and. Certain cynomolgus macaque MCH2R polynucleotides comprise at least 930, at least 975 or 1023 consecutive nucleotides of a cynomolgus macaque MCH2R nucleotide sequence provided herein (SEQ ID NO:1, 3 or 5). SEQ ID NOs:1 and 5 encode MCH2R version A—SEQ ID NO:5 is a native cynomolgus macaque MCH2R version A, and the sequence provided in SEQ ID NO:1 contains two single nucleotide substitutions relative to SEQ ID NO:5 (at positions 426 and 435). These substitutions do not affect the encoded amino acid sequence. The sequence provided in SEQ ID NO:3 encodes MCH2R version B, and differs from the native cynomolgus macaque MCH2R sequence due to the same substitutions at positions 426 and 435 (as well as the substitution at position 113 that results in a Leu at residue 38).

Canine MCH2R polynucleotides generally encode at least a portion of a native canine MCH2R protein. Typically, such polynucleotides encode at least 70, at least 100, at least 300, at least 315 or 330 consecutive amino acids of a native canine MCH2R protein sequence provided in SEQ ID NO:7. For less than full length MCH2R sequences, deletions may be made at any point in the naturally-occurring sequence, such as at the 3' end. Certain canine MCH2R polynucleotides comprise at least 210, at least 30, at least 900, at least 945 or 993 consecutive nucleotides of the canine MCH2R polynucleotide sequence provided herein (SEQ ID NO:6).

The present invention also provides polynucleotides that encode chimeric MCH2R polypeptides as described herein. As noted above, polynucleotides encoding such chimeras may comprise native or non-native sequences. Certain representative polynucleotides encode a chimeric MCH2R polypeptide as provided in any one of SEQ ID NOs:15–28, 33 and 34, herein. Sequences that may be used to construct such polynucleotides are provided herein (macaque MCH2R and canine MCH2R), and in the literature (e.g., GenBank Accession Number M88461 (SEQ ID NO:31 herein) for human $NPY_1$ receptor sequence; Accession Number Y00106 (SEQ ID NO:32 herein) for human beta-2 adrenergic receptor; co-pending U.S. patent application Ser. No. 10/126,764 (SEQ ID NO:30 herein) for macaque MCH1R). Specific coding sequences that may be used for the construction of the chimeras will be readily determined by those of ordinary skill in the art from the amino acid sequences provided herein. Chimeric sequences may be generated using standard recombinant techniques.

Polynucleotides complementary to the MCH2R polynucleotide sequences described herein (or portions thereof) are also encompassed by the present invention. Such polynucleotides include, for example, PCR products and restriction fragments, and may find use as probes or primers. Probes may be labeled with a variety of reporter groups, such as radionuclides and enzymes. Complementary polynucleotides generally hybridize to a MCH2R polynucleotide under stringent conditions. Stringent conditions include, for example, hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C.). For short oligonucleotide probes, washing may be performed in 6×SSC/0.05% sodium pyrophosphate at 37° C. (for 14-base oligos), 48° C. (for 17-base oligos), 55° C. (for 20-base oligos), and 60° C. (for 23-base oligos). Other stringent conditions include overnight hybridization at 42° C. in a solution comprising: 50% formamide, 5×SSC (150 mM NaCl, 15 mM trisodium citrate), 50 mM sodium phosphate (pH 7.6), 5×Denhardt's solution, 10% dextran sulfate, and 20 μg/mL denatured, sheared salmon sperm DNA, followed by washing the filters in 0×SSC at about 65° C. A complementary sequence may, for example, be complementary to a sequence that encodes at least 310, at least 325 or 340 consecutive amino acids of a cynomolgus macaque MCH2R protein sequence, such as that provided in SEQ ID NO:2 or SEQ ID NO:4, or may be complementary to a sequence that encodes at least 70, at least 100, at least 300, at least 315 or 330 consecutive amino acids of a canine MCH2R protein sequence, such as that provided in SEQ ID NO:7.

It will be appreciated by those of ordinary skill in the art that, as a result of the degeneracy of the genetic code, there are many nucleotide sequences that encode the polypeptides provided herein. Some of these polynucleotides bear minimal homology to the nucleotide sequence of any naturally occurring gene. Nonetheless, polynucleotides that vary due to differences in codon usage are specifically contemplated by the present invention. Additionally, it will be apparent that sequence changes may be made in the non-coding regions of the polynucleotides without altering the amino acid sequence of the protein product. Polynucleotides that encode amino acid sequences with up to 15 (preferably no more than 10, more preferably no more than 5) amino acid substitutions relative to a native sequence, as discussed above, are also provided herein.

Polynucleotides provided herein may further comprise additional sequences. For example, an optimized translation initiation sequence (Kozak sequence) may be added to the 5' terminus. A primer comprising the Kozak sequence is provided in SEQ ID NO:12. In-frame additions of sequences encoding antibody recognition sites may also be included. Such amino acid sequences include, but are not limited to, the His-6× (hexa-histicline) epitope (SEQ ID NO:13) which is specifically bound by the Monoclonal Anti-polyhistidine Clone HIS-1 monoclonal antibody (Sigma, St. Louis No.H1029), and the FLAG epitope (SEQ ID NO:14) which is specifically bound by the FLAG-M2 monoclonal antibody (Sigma, St. Louis No. F3165). Such modifications may be readily introduced using routine methods or by using prepared kits, such as the Sigma Mammalian FLAG Expression Kits (Sigma, St. Louis; e.g., Nos. FL-MA and FL-MC). Preferably, fusions are made as in-frame amino- (N-) or carboxy- (C-) terminal fusions. C-terminal fusions are generally less prone to interfere with membrane insertion of the fusion protein, and are commonly used when properly membrane-inserted fusion proteins (e.g., proteins retaining receptor signal transduction function) are desired.

Polynucleotides are preferably "isolated" (i.e., represent at least 10% of total nucleic acid molecules, preferably at least 20% and more preferably at least 50% of total nucleic acid molecules, within a sample or preparation). Unless otherwise specified, a polynucleotide comprising a given sequence may be of any length.

Polynucleotides may be prepared using any of a variety of well known techniques. For example, polynucleotides (or portions thereof) may be amplified via polymerase chain reaction (PCR), using sequence-specific primers designed based on the sequences provided herein, which may be purchased or synthesized. Portions of a desired polynucleotide obtained using PCR may be assembled into a single contiguous sequence by ligating suitable fragments, using well known techniques. Alternatively, an amplified portion may be used to isolate a full length gene from a suitable library (e.g., one or more brain regions such as amygdala, temporal cortex, frontal cortex and/or parietal cortex) using well known hybridization techniques. Within such techniques, a library (cDNA or genomic) is screened using one or more polynucleotide probes or primers corresponding to a portion of the desired sequence. Such a library may be size-selected for larger molecules; random primed libraries may be used to obtain 5' regions of genes. It will be apparent that primers designed based on the sequences provided herein may be used to obtain polynucleotides encoding MCH2R from other species.

RNA molecules may be generated by in vitro or in vivo transcription of DNA sequences encoding an MCH2R polypeptide, provided that the DNA is incorporated into a vector with a suitable RNA polymerase promoter (such as T7 or SP6). For example, antisense RNA may be generated from suitable cDNA constructs that have been introduced into cells or tissues to facilitate the production of antisense RNA.

Polynucleotides containing nucleotide substitutions, additions and/or deletions may generally be prepared by any standard method, including chemical synthesis by, for example, solid phase phosphoramidite chemical synthesis. Modifications in a polynucleotide sequence may also be introduced using standard mutagenesis techniques, such as oligonucleotide-directed site-specific mutagenesis.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication that is functional in at least one organism, convenient restriction endonuclease sites and one or more selectable markers. Other elements will depend upon the desired use, and will be apparent to those of ordinary skill in the art.

Expression Systems

An expression vector is a vector for recombinant expression of an MCH receptor polypeptide, comprising an MCH receptor polynucleotide operatively linked to the necessary nucleotide sequences for expression (e.g., a suitable promoter and, if necessary, a terminating signal). A promoter is a nucleotide sequence (typically located 5' to the MCH receptor polynucleotide) that directs the transcription of adjacently linked coding sequences. A terminating signal may be a stop codon to end translation and/or a transcription termination signal. Additional regulatory element(s) (e.g., enhancer elements) may also be present within an expression vector. Such a vector is preferably a plasmid or viral vector. Techniques for incorporating DNA into such vectors are well known to those of ordinary skill in the art.

Preferably, an expression vector further comprises a selectable marker, which confers resistance to a selection. This allows cells to stably integrate the vector into their chromosomes and grow to form foci, which in turn can be cloned and expanded into cell lines. A number of selection systems can be used. For example, the hypoxanthine-guanine phosphoribosyltransferase, adenine phosphoribosyltransferase and herpes simplex virus thymidine kinase genes can be employed in hgprt⁻, aprt⁻ or tk⁻ cells, respectively. Also, anti-metabolite resistance can be used as the basis of selection for genes such as: dhfr, which confers resistance to methotrexate; gpt, which confers resistance to mycophenolic acid; neo, which confers resistance to the aminoglycoside G-418); hygro, which confers resistance to hygromycin; and puro, which confers resistance to puromycin.

Expression systems that may be used in the practice of certain aspects of the present invention include, but are not limited to, (a) insect cell systems infected with recombinant virus expression vectors (e.g., baculovirus) comprising one or more polynucleotides provided herein and (b) mammalian cell systems (e.g., COS, CHO, BHK, HEK 293, VERO, HeLa, MDCK, WI38 and NIH 3T3 cells) harboring recombinant expression constructs comprising one or more polynucleotides provided herein.

Mammalian vectors should contain promoters, preferably derived from the genome of mammalian cells (for example, a metallothionein actin or phosphoglycerate kinase promoter) or from mammalian viruses (for example, the adenovirus late promoter, a CMV promoter and the vaccinia virus 7.5K promoter). One suitable mammalian expression vector is the PCDNA3.1 vector (INVITROGEN, Carlsbad, Calif.). In adenoviral expression vectors, the MCH receptor polynucleotide may be ligated to an adenovirus transcription/translation control complex such as the late promoter and tripartite leader sequence. Specific initiation signals (e.g., the ATG initiation codon and adjacent sequences such as ribosome binding sites) may also be required for efficient translation of inserted nucleic acid molecules. The efficiency of expression may be further enhanced by the inclusion of appropriate transcription enhancer elements, transcription terminators, etc. The recombinant gene may then be inserted in the adenovirus genome by in vitro or in vivo recombination. Insertion in a non-essential region of the viral genome (for example, region E1 or E3) will result in a recombinant virus that is viable and capable of expressing an MCH receptor polypeptide in infected.

Another representative expression system is an amphibian oocyte system in which MCH2R RNA is introduced into an oocyte. Preferably the amphibian is a frog, most preferably the African clawed frog, Xenopus laveis. One suitable expression vector for expression in amphibian oocytes is the pBLUESCRIPT SK⁻ vector (STRATAGENE Cloning Systems, La Jolla, Calif.). Typically such vectors are used to generate MCH receptor polypeptide-encoding RNAs in in vitro transcription systems, which RNAs are then injected into the oocytes to induce expression of the encoded protein.

An insect system utilizing a baculovirus such as *Autographa californica* nuclear polyhedrosis virus (AcNPV) can be used to express the MCH receptor polypeptides provided herein. The virus grows in insect cells such as *Spodoptera frugiperda* cells. The coding sequence encoding the MCH receptor polypeptide is typically inserted (e.g., ligated) into non-essential regions of the virus (for example into the polyhedrin gene) and placed under control of an AcNPV promoter (for example the polyhedrin promoter). Preferably, the successful introduction of the insert will result in inactivation of a viral gene. For example, when targeted into the polyhedrin gene, the successful incorporation of the insert will inactivate that gene and result in production of non-occluded recombinant virus (i.e., virus lacking the proteinaceous coat coded for by the polyhedrin gene). The resulting recombinant viruses are then used to infect insect cells, preferably *Spodoptera frugiperda* cells, in which the inserted coding sequence is expressed. A variety of kits for use in the preparation of an insect expression system are commercially available.

Host cells transformed or transfected with an expression vector comprising an MCH receptor polynucleotide, and capable of expressing an MCH receptor polypeptide, are further provided herein. Such cells may be prepared using standard transformation techniques. Stable expression is generally preferred, although transient expression systems may be suitable for certain uses. Following the introduction of the vector (often following incubation in a non-selective medium to allow for recovery from the stress of vector introduction), engineered cells may be grown in a selective medium.

Assays

MCH receptor polynucleotides and polypeptides may be used within a variety of assays to screen for and characterize compounds that modulate MCH receptor function. Such assays typically involve contacting a compound with transfected host cells or membrane preparations as described above, and subsequently detecting (a) binding of the compound to the cells or membranes (direct binding assays—e.g., via surface plasmon resonance, using a device available from BIAcor AB, Sweden); (b) an effect of the compound on labeled ligand (e.g., radiolabeled MCH) binding to the cells or membranes (competitive binding assays); or (c) an effect on a cellular receptor response to MCH (functional assays). Compounds may be any substance, but are preferably small organic, non-peptide molecules. Compounds identified using such assays are useful, for example, as tools for receptor mapping and as pharmaceutical agents.

One suitable competitive binding assay is provided in Example 4. In such an assay, a test compound is used as a cold displacer. Briefly, an MCH receptor-containing membrane preparation (e.g., prepared from transfected HEK293 cells) is contacted (incubated) with labeled (e.g., $^{125}$I) MCH and unlabeled test compound. Unbound MCH is then removed (e.g., by washing) and remaining bound label is then detected. Incubation with a compound that detectably modulates MCH binding to MCH receptor will result in a decrease or increase in the amount of label bound to the MCH receptor preparation, relative to the amount of label bound in the absence of the compound. Preferably, such a compound will exhibit a K, at an MCH receptor of less than 1 micromolar, more preferably less than 500 nM, 100 nM, 20 nM or 10 nM, within a ligand binding assay performed as described in Example 4.

Functional assays use transfected host cells as substrates and measure cellular responses to contact with a test compound. Within such assays, a compound may act as an agonist, mediating a cell-based response when contacted with a cell-surface MCH receptor, or as an antagonist, inhibiting the response of cell-surface MCH receptor to MCH. A representative $Ca^{2+}$ mobilization assay suitable for detecting such responses is set forth below as Example 5. Within such an assay, MCH receptor modulating activity of a test compound is detected by: (a) incubating (i.e., contacting) transgenic (e.g., transformed or transfected) cells with a compound; (b) detecting a level of $Ca^{2+}$ in the contacted cells; and (c) comparing the level of $Ca^{2+}$ with a level of $Ca^{2+}$ detected in control cells that are incubated in the absence of test compound. Preferably, within such assays, the transgenic cells are initially contacted with an indicator of intracellular $Ca^{2+}$ concentration and then washed. The compound is then contacted with the washed cells, and the level of $Ca^{2+}$ detected by quantifying $Ca^{2+}$-concentration-dependent changes in the properties of the indicator of intracellular $Ca^{2+}$. The level of calcium detected in the presence of candidate compound is preferably at least 2-fold greater than the level detected in the absence of candidate compound (i.e., in control cells that are contacted with the indicator of intracellular $Ca^{2+}$ concentration, but not with the test compound).

MCH receptor antagonist activity may be detected using calcium mobilization assays performed in the presence of a known MCH receptor agonist (e.g., MCH). MCH receptor agonist is preferably added to test and control cells just prior to detecting intracellular $Ca^{2+}$ concentration. Preferably, the concentration of intracellular Ca in the agonist-contacted test cell is significantly less (to the $p \leq 0.05$ level, as measured using a parametric test of statistical significance) than the concentration of intracellular $Ca^{2+}$ in the agonist-contacted control cell.

Compounds identified using such assays may be used to treat a disease or disorder associated with MCH receptor activation, such as eating disorders (e.g., obesity and bulimia nervosa), sexual disorders, diabetes, heart disease and stroke. Patients may include humans, companion animals (such as dogs) and livestock animals.

The following Examples are offered by way of illustration and not by way of limitation.

EXAMPLES

Example 1

MCH2R Polynucleotide Preparation

This Example illustrates the isolation of representative MCH2R polynucleotides from monkey and dog.

RNA was isolated from cynomolgus macaque amygdala, temporal cortex and frontal cortex using Trizol Reagent (Life Technologies, Gaithersburg, Md.). cDNA was prepared using PowerScript Reverse Transcriptase (Clontech). Both steps were performed according to the manufacturer's instructions.

Cynomolgus macaque MCH2R cDNAs were obtained using PCR, with the following primers:

```
5'forward outer primer
5'-TCCCTGGAAA GGCCACGAAC AATG-3'   (SEQ ID NO:8)

879R reverse primer
5'-CAGCACCAGC ACCATCTTTG TC-3'     (SEQ ID NO:9)

509 forward primer
5'-TTGCCCTCGT CCAACCATTT CG-3'     (SEQ ID NO:10)

3'reverse outer primer
5'-GGTGATCCAT GTACTTTCCT A-3'      (SEQ ID NO:11)
```

PCR was performed using the Advantage-GC cDNA PCR Kit (Clontech Laboratories Palo Alto, Calif.) in 50 microliter reactions containing: 10 microliters GC Melt, 10 microliters 5×PCR reaction buffer, 1 microliter 50×dNTP Mix (10 mM each), 12.5 pmoles forward and reverse primers, 1 microliter Advantage-GC cDNA Polymerase Mix (SOX), 1 microliter cynomolgus macaque RT product.

Touchdown PCR was performed as follows:
94° C. for 3 minutes
20 cycles of:
  94° C. for 30 seconds
  55° C. to 45° C. in 0.5° C. intervals for 30 seconds
  68° C. for 30 seconds
20 cycles of:
  94° C. for 30 seconds
  50° C. for 30 seconds
  68° C. for 30 seconds After sequencing multiple 5' and 3' PCR clones, the sequence shown in SEQ ID NO:5 was identified as a cynomolgus macaque MCH2R sequence. A polymorphism consisting of one base change leading to an amino acid change (Pro→Leu at position 38) was also identified.

Overlapping 5' and 3' clones were subsequently combined to form full coding sequences. Clone A (SEQ ID NO:1) encodes an MCH2R with a Pro at position 38 (SEQ ID NO:2), and clone B (SEQ ID NO:3) encodes an MCH2R with a Leu at position 38 (SEQ ID NO:4). Other than the presence of the polymorphism in clone B, clones A and B differ from the sequence shown in SEQ ID NO:5 only in the substitution of G's for A's at positions 426 and 435. These substitutions do not affect the encoded protein. An additional 5' macaque primer (SEQ ID NO:12) containing an optimized translation initiation sequence (Kozak sequence) was used to place the Kozak site on the cDNAs.

The canine MCH2R sequence was obtained using the reactions, conditions and primers described above, except that the template was prepared using RNA isolated from canine amygdala, temporal cortex and parietal cortex. As described above, 5' and 3' clones were combined to form the full coding region (SEQ ID NO:6). The encoded amino acid sequence is provided in SEQ ID NO:7.

The amino acid sequences of cynomolgus macaque MCH2R clones A and B, and canine MCH2R, are shown in FIG. 1, aligned with the human MCH2R sequence (SEQ ID NO:29).

Example 2

Preparation of Host Cells Expressing MCH2R Polypeptides

This Example illustrates the expression of representative MCH2R polynucleotides from macaque and dog in transfected host cells.

PCR products were subcloned directly into pcDNA 3.1/V5-His-TOPO (Invitrogen). The final confirmed PCR products were ligated together directly in this vector or in pcDNA 3.1 (Invitrogen). A 5' sequence that includes an optimized translation initiation sequence (Kozak sequence; SEQ ID NO: 12) was inserted at the 5' end of the full length cDNA.

HEK 293 cells were transiently or stably transfected via standard calcium phosphate precipitation procedures with the MCH2R expression vector. For transient transfection, cells were grown to confluency at 37° C., 5% $CO_2$, for approximately 48–72 hours in DMEM high glucose culture medium (catalog #10-017-CV, MEDIATECH, Herndon, Va.) supplemented with 10% fetal bovine serum, 25 mM HEPES. Cells could then be used directly within assays. For stable expression, cells were grown under the conditions described above (with the addition of 500 μg/ml G418) for 2–3 weeks. Single selected colonies were then chosen to generate a stable cell line.

CHO (Chinese Hamster Ovary) cells were also transfected via standard calcium phosphate precipitation procedures with the MCH2R expression vector. For transient transfection, cells were grown to confluency at 37° C., 5% $CO_2$, approximately 48–72 hours, in Ham's F12 culture medium (catalog #10-080-CV, MEDIATECH, Herndon, Va.) supplemented with 10% fetal bovine serum, 25 mM HEPES. Cells could then be used directly within assays. For stable expression, cells were grown under the conditions described above (with the addition of 500 μg/ml G418) for 2–3 weeks. Single selected colonies were then chosen to generate a stable cell line.

Example 3

Cell Membrane Preparations

This Example illustrates the isolation of cell membrane preparations comprising MCH2R polypeptides, for use within a variety of binding and activity assays.

Transfected HEK 293 cell pellets stored frozen at −80° C. are thawed by addition of wash buffer (25 mM Hepes with 1.0 mM $CaCl_2$, 5.0 mM $MgCl_2$, 120 mM NaCl, PH 7.4) and homogenized for 30 seconds using a BRINKMAN POLYTRON, setting 5. Cells are then centrifuged for 10 minutes at 48,000×g. The supernatant is discarded and the pellet is resuspended in fresh wash buffer, and homogenized again. The protein concentration of the resulting membrane preparation is measured using the Bradford protein assay (Bio-Rad Laboratories, Hercules, Calif.). By this measure, a 1-liter culture of cells typically yields 50–75 mg of total membrane protein.

Example 4

MCH2R Ligand Binding Assays

This Example illustrates the use of MCH2R-containing membrane preparations within binding assays to monitor the ability of cells expressing MCH receptors to bind MCH or to screen for MCH2R agonists and antagonists.

Purified membranes from HEK 293 cells expressing MCH2R are prepared as described above. The membrane homogenate is centrifuged as before and resuspended to a protein concentration of 333 μg/ml in binding buffer (Wash buffer +0.1% BSA and 1.0 uM final conc. phosphoramidon) for an assay volume of 50 μg membrane protein/150 μl binding buffer. Phosphoramidon is from SIGMA BIO-CHEMICALS, St. Louis, Mo. (cat#R-7385).

Ligand binding assays are performed at room temperature by combining 150 μl of MCH2R-containing membranes in binding buffer, prepared as described above, 50 μl $^{125}$I-Tyr MCH in binding buffer and 50 μl binding buffer. $^{125}$I-Tyr MCH (specific activity=2200 Ci/mMol) is purchased from NEN, Boston, Mass. (Cat #NEX 373) and is diluted in binding buffer to provide a final assay concentration of 30 pM.

Competition binding assays for screening test compounds are performed at room temperature in Falcon 96 well round bottom polypropylene plates. To each assay well is added 150 μl of MCH2R-containing membranes in binding buffer, prepared as described above, 50 μl $^{125}$I-Tyr MCH in binding buffer, 50 μl binding buffer and 2 μl test compound in DMSO.

Non-specific binding is defined as the binding measured in the presence of 1 μM unlabeled MCH. MCH is purchased from BACHEM U.S.A., King of Prussia, Pa. (cat #H-1482). To each assay well used to determine non-specific MCH binding is added: 150 μl of MCH2R-containing membranes in binding buffer, 50 μl $^{125}$I-Tyr MCH in binding buffer, unlabeled MCH in 25 μl binding buffer, and 25 μl binding buffer.

Assay plates are incubated for 1 hour at room temperature. Membranes are harvested onto WALLAC glass fiber filters (PERKIN-ELMER, Gaithersburg, Md.) which are pre-soaked with 1.0% PEI (polyethyleneimine) for 2 hours prior to use. Filters are allowed to dry overnight then counted in a WALLAC 1205 BETA PLATE counter after addition of WALLAC BETA SCINT scintillation fluid.

For saturation binding the concentration of $^{125}$I-Tyr MCH is varied from 7–1,000 pM. Typically 11 concentration points are collected per saturation binding curve. Equilibrium binding parameters are determined by fitting the allosteric Hill equation to the measured values with the aid of the computer program FitP™ (BIOSOFT, Ferguson, Mo.).

Example 5

MCH2R Calcium Mobilization Assay

This Example illustrates the use of MCH2R-expressing cells within functional assays to monitor the response of cells expressing MCH receptors to MCH or to screen for MCH2R agonists and antagonists.

CHO or HEK 293 cells stably transfected with an MCH2R receptor expression vector as described above are grown to a density of 30,000 cells/well in FALCON black-walled, clear-bottomed 96-well plates (#3904, BECTON-DICKINSON, Franklin Lakes, N.J.). Prior to running the assay the culture medium is emptied from the 96 well plates. Fluo-3 calcium sensitive dye (Molecular Probes, Eugene, Oreg.) is added to each well (dye solution: 1 mg FLUO-3 AM, 440 μl DMSO and 440 μl 20% pluronic acid in DMSO; diluted 8.8 μl/ml with KRH; 50 μl diluted solution added per well). Plates are covered with aluminum foil and incubated at 37° C. for 1–2 hours. After the incubation the dye solution is emptied from the plates, cells are washed once in 100 μl KRH buffer (0.05 mM KCl, 0.115 M NaCl, 9.6 mM $NaH_2PO_4$, 0.01 mM $MgSO_4$, 1 mM probenecid (Sigma), 25 mM HEPES, pH 7.4) to remove excess dye; after washing, 80 μl KRH buffer is added to each well.

Prior to evaluating a test compound, the $EC_{50}$ of MCH is determined. An additional 20 μl of KRH buffer and 1 μl DMSO is added to each well of cells, prepared as described immediately above. 100 μl human MCH in KRH buffer is automatically transferred by a FLIPR™ plate reader (Molecular Devices, Sunnyvale, Calif.) to each well, and fluorescence response is monitored by excitation at 480 nM and emission at 530 nM. An 8-point concentration response curve, with final MCH concentrations of 1 nM to 3 μM, is used to determine MCH $EC_{50}$. FIG. 2 illustrates the response of HEK 293 cells expressing MCH2R to MCH in this assay.

In order to measure the ability of a test compound to antagonize the response of cells expressing MCH2R receptors to MCH, Test compounds are dissolved in DMSO, diluted in 20 μl KRH buffer, and added to cells prepared as described above. The 96 well plates containing prepared cells and test compounds are incubated in the dark, at room temperature for 0.5 to 6 hours. It is important that the incubation not continue beyond 6 hours. Just prior to determining the fluorescence response, 100 μl human MCH diluted in KRH buffer to $2 \times EC_{50}$ is automatically added by the FLIPR instrument to each well of the 96 well plate for a final sample volume of 200 μl and a final MCH concentration of $EC_{50}$. The final concentration of test compounds in the assay wells is between 1 μM and 5 μM. Typically, cells exposed to one $EC_{50}$ of MCH exhibit a fluorescence response of about 10,000 Relative Fluorescence Units. Antagonists of the MCH receptor exhibit a response that is significantly less than that of the control cells to the $p \leq 0.05$ level, as measured using a parametric test of statistical significance. Antagonists of the MCH receptor decrease the fluorescence response relative to control cells by at least 20%, preferably by at least 50%, and most preferably by at least 80%.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated polynucleotide encoding a chimeric MCH2R polypeptide, wherein the polypeptide comprises the cynomolgus macaque sequence recited in SEQ ID NO:2 or the cynomolgous macaque sequence recited in SEQ ID NO:4 wherein one or more of the intracellular loop 3, N-terminal domain and C-terminal domain of said cynomolgous macaque sequence is replaced with a corresponding domain of MCH1R, NPY$_1$ receptor, beta-2-adrenergic receptor, human MCH2R or canine MCH2R.

2. An expression vector comprising a polynucleotide according to claim 1.

3. An expression vector according to claim 2, wherein the vector is a plasmid.

4. an expression vector according to claim 2, wherein the vector is a viral vector.

5. a transgenic cell transformed or transfected with an expression vector according to claim 2.

6. A transgenic cell according to claim 5, wherein the cell is a mammalian cell.

7. A transgenic cell according to claim 5, wherein the cell is an oocyte.

8. A cell membrane preparation isolated from transgenic cell according to claim 5.

9. A cell membrane preparation according to claim 8, wherein the cell membrane preparation exhibits MCH1R ligand binding activity that is at lent 2-fold greater than MCH1R ligand binding activity exhibited by a control membrane preparation isolated from untransformed cells.

10. A method for determining MCH receptor binding activity of a compound, comprising the steps of:
   (a) contacting a compound with a cell membrane preparation according to claim 8; and
   (b) detecting binding of the compound to the cell membrane preparation, and therefrom determining an MCH receptor binding activity for the compound.

11. A method according to claim 10, wherein binding is detected by measuring the ability of the compound to compete with detectably labeled MCH for binding to the membrane preparation.

12. A method for detecting MCH receptor modulating activity of a compound, comprising the steps of:
   (a) contacting transgenic cells according to claim 5 with a compound;
   (b) detecting a level of $Ca^{2+}$ in the contacted cells; and
   (c) comparing the detected level of $Ca^{2+}$ with a level of $Ca^{2+}$ detected in control transgenic cells according to claim 7, in the absence of the compound, and therefrom detecting MCH receptor modulating activity or the compound.

13. A method according to claim 12, wherein prior to the step of contacting with compound, the transgenic cells are:
   (i) contacted with an indicator of intracellular $Ca^{2+}$ concentration to yield indicator-loaded cell; and
   (ii) washed to yield washed indicator-loaded cells;
   and wherein the level of calcium is detected by quantifying a $Ca^{2+}$ concentration-dependent change in a property of the indicator of intracellular $Ca^{2+}$ concentration.

14. A method according to claim 12 wherein the level of calcium detected in the presence of compound is at least 2-fold greater than the level detected in the absence of compound.

15. An isolated polynucleotide according to claim 1, wherein the chimeric polypeptide has a sequence recited in any one of SEQ ID NOs: 15–28, 33 or 34.

* * * * *

UNITED STATES PATENT AND TRADEMARK OFFICE
CERTIFICATE OF CORRECTION

PATENT NO. : 7,141,391 B2 Page 1 of 1
APPLICATION NO. : 10/291990
DATED : November 28, 2006
INVENTOR(S) : Michele Bennet Kinrade et al.

It is certified that error appears in the above-identified patent and that said Letters Patent is hereby corrected as shown below:

Column 70, line 1 of claim 4, "an" should be changed to --An--

Column 70, line 1 of claim 5, "a" should be changed to --A--

Column 70, line 3 of claim 9, "lent" should be changed to --least--

Column 72, line 9 of claim 12, "or" should be changed to --of--

Column 72, line 4 of claim 13, "cell" should be changed to --cells--

Signed and Sealed this

Seventeenth Day of July, 2007

JON W. DUDAS
*Director of the United States Patent and Trademark Office*